United States Patent
Zink et al.

(10) Patent No.: US 10,351,827 B2
(45) Date of Patent: Jul. 16, 2019

(54) METHOD FOR DIFFERENTIATING INDUCED PLURIPOTENT STEM CELLS INTO RENAL PROXIMAL TUBULAR CELL-LIKE CELLS

(71) Applicant: AGENCY FOR SCIENCE, TECHNOLOGY AND RESEARCH, Singapore (SG)

(72) Inventors: Daniele Zink, Singapore (SG); Jackie Y. Ying, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/035,739

(22) PCT Filed: Nov. 11, 2014

(86) PCT No.: PCT/SG2014/000529
§ 371 (c)(1),
(2) Date: May 10, 2016

(87) PCT Pub. No.: WO2015/069192
PCT Pub. Date: May 14, 2015

(65) Prior Publication Data
US 2016/0281062 A1 Sep. 29, 2016

(30) Foreign Application Priority Data
Nov. 11, 2013 (SG) .................... 2013083415

(51) Int. Cl.
| | |
|---|---|
| *C12N 5/00* | (2006.01) |
| *C12N 5/02* | (2006.01) |
| *C12N 5/071* | (2010.01) |
| *A61K 35/545* | (2015.01) |
| *A61K 35/22* | (2015.01) |
| *A61L 27/36* | (2006.01) |
| *A61L 27/38* | (2006.01) |
| *A61L 27/54* | (2006.01) |
| *A61L 27/58* | (2006.01) |

(52) U.S. Cl.
CPC ............ *C12N 5/0686* (2013.01); *A61K 35/22* (2013.01); *A61K 35/545* (2013.01); *A61L 27/3604* (2013.01); *A61L 27/3641* (2013.01); *A61L 27/3839* (2013.01); *A61L 27/3895* (2013.01); *A61L 27/54* (2013.01); *A61L 27/58* (2013.01); *A61L 2300/414* (2013.01); *A61L 2300/64* (2013.01); *A61L 2430/26* (2013.01); *A61L 2430/40* (2013.01); *C12N 2501/155* (2013.01); *C12N 2501/727* (2013.01); *C12N 2506/45* (2013.01); *C12N 2533/90* (2013.01)

(58) Field of Classification Search
CPC .................................................. C12N 5/0686
See application file for complete search history.

(56) References Cited

U.S. PATENT DOCUMENTS 8,481,316 B2 * 7/2013 Schumacher ........ C12N 5/0686
435/366

OTHER PUBLICATIONS

Narayanan (Feb. 6, 2013, Kidney International, 83:593-603).*
Robinton (2012, Nature, 481: 295-305).*
Kandasamy, 2015, Nature Scientific Reports, 5:123337, 1.*
Fisel, P., Renner, O., Nies, A.T., Schwab, M. & Schaeffeler, E. Solute carrier transporter and drug-related nephrotoxicity: the impact of proximal tubule cell models for preclinical research. Expert Opin Drug Metab Toxicol 10, 395-408 (2014).
Tiong, H.Y. et al. Drug-Induced Nephrotoxicity: Clinical Impact and Preclinical in Vitro Models. Mol Pharm 11, 1933-1948 (2014).
Naughton, C.A. Drug-induced nephrotoxicity. Am Fam Physician 78, 743-750 (2008).
Redfern, W.S. Impact and frequency of different toxicities throughout the pharmaceutical life cycle. The Toxicologist 114, 1081 (2010).
Li, Y. et al. An in vitro method for the prediction of renal proximal tubular toxicity in humans. Toxicol Res 2, 352-362 (2013).
Narayanan, K. et al. Human embryonic stem cells differentiate into functional renal proximal tubular-like cells. Kidney Int 83, 593-603 (2013).
Li, Y. et al. Identification of nephrotoxic compounds with embryonic stem cell derived human renal proximal tubular-like cells. Mol Pharm 11, 1982-1990 (2014).
Kang, M. & Han, Y.M. Differentiation of human pluripotent stem cells into nephron progenitor cells in a serum and feeder free system. PLoS One 9, e94888 (2014).
Lam, A.Q. et al. Rapid and Efficient Differentiation of Human Pluripotent Stem Cells into Intermediate Mesoderm That Forms Tubules Expressing Kidney Proximal Tubular Markers. J Am Soc Nephrol 25, 1211-1225 (2014).
Mae, S. et al. Monitoring and robust induction of nephrogenic intermediate mesoderm from human pluripotent stem cells. Nat Commun 4, 1367 (2013), pp. 1-11.
Taguchi, A. et al. Redefining the in vivo origin of metanephric nephron progenitors enables generation of complex kidney structures from pluripotent stem cells. Cell Stem Cell 14, 53-67 (2014).
Takasato, M. et al. Directing human embryonic stem cell differentiation towards a renal lineage generates a self-organizing kidney. Nat Cell Biol 16, 118-126 (2014).

(Continued)

*Primary Examiner* — Valarie E Bertoglio
(74) *Attorney, Agent, or Firm* — Womble Bond Dickinson (US) LLP

(57) ABSTRACT

There is provided a method of differentiating an induced pluripotent stem cell (iPSC) into a renal proximal tubular cell (PTC)-like cell. The method comprises culturing an undifferentiated iPSC in a renal epithelial cell culture medium in the presence of one or more extracellular matrix (ECM) molecules, bone morphogenic protein 2 (BMP2) and bone morphogenic protein 7 (BMP7), for a period of from about 8 to about 10 days, under conditions sufficient to induce differentiation of the iPSC into a PTC-like cell. A cell population of differentiated PTC-like cells is also provided, as well as uses and methods of use of the cell population.

6 Claims, 10 Drawing Sheets

Specification includes a Sequence Listing.

(56) References Cited

OTHER PUBLICATIONS

Xia, Y. et al. Directed differentiation of human pluripotent cells to ureteric bud kidney progenitor-like cells. Nat Cell Biol 15, 1507-1515 (2013).

Showell, C., Binder, O. & Conlon, F.L. T-box genes in early embryogenesis. Dev Dyn 229, 201-218 (2004).

Mugford, J.W., Sipila, P., McMahon, J.A. & McMahon, A.P. Osr1 expression demarcates a multi-potent population of intermediate mesoderm that undergoes progressive restriction to an Osr1-dependent nephron progenitor compartment within the mammalian kidney. Dev Biol 324, 88-98 (2008).

Kobayashi, A. et al. Six2 defines and regulates a multipotent self-renewing nephron progenitor population throughout mammalian kidney development. Cell Stem Cell 3, 169-181 (2008).

Kreidberg, J.A. WT1 and kidney progenitor cells. Organogenesis 6, 61-70 (2010).

Vainio, S. & Lin, Y. Coordinating early kidney development: lessons from gene targeting. Nat Rev Genet 3, 533-543 (2002).

Mugford, J.W., Sipila, P., Kobayashi, A., Behringer, R.R. & McMahon, A.P. Hoxd11 specifies a program of metanephric kidney development within the intermediate mesoderm of the mouse embryo. Dev Biol 319, 396-405 (2008).

Thomson, R.B. et al. Isolation and cDNA cloning of Ksp-cadherin, a novel kidney specific member of the cadherin multigene family. J Biol Chem 270, 17594-17601 (1995).

Maunsbach, A.B. et al. Aquaporin-1 water channel expression in human kidney. J Am Soc Nephrol 8, 1-14 (1997).

Hanigan, M.H. & Frierson, H.F., Jr. Immunohistochemical detection of gammaglutamyl transpeptidase in normal human tissue. J Histochem Cytochem 44, 1101-1108 (1996).

Elberg, G., Guruswamy, S., Logan, C.J., Chen, L. & Turman, M.A. Plasticity of epithelial cells derived from human normal and ADPKD kidneys in primary cultures. Cell Tissue Res 331, 495-508 (2008).

Kusaba, T., Lalli, M., Kramann, R., Kobayashi, A. & Humphreys, B.D. Differentiated kidney epithelial cells repair injured proximal tubule. Proc Natl Acad Sci U S A 111, 1527-1532 (2014).

Fan, J.M. et al. Transforming growth factor-beta regulates tubular epithelial myofibroblast transdifferentiation in vitro. Kidney Int 56, 1455-1467 (1999).

Zhang, H. et al. Generation of easily accessible human kidney tubules on two dimensional surfaces in vitro. J Cell Mol Med 15, 1287-1298 (2011).

Palena, C. et al. The human T-box mesodermal transcription factor Brachyury is a candidate target for T-cell-mediated cancer immunotherapy. Clin Cancer Res 13, 2471-2478 (2007).

Biber, J., Hernando, N., Forster, I. & Murer, H. Regulation of phosphate transport in proximal tubules. Pflugers Arch 458, 39-52 (2009).

Burckhardt, G. Drug transport by Organic Anion Transporters (OATs). Pharmacol Ther 136, 106-130 (2012).

Miller, R.P., Tadagavadi, R.K., Ramesh, G. & Reeves, W.B. Mechanisms of Cisplatin nephrotoxicity. Toxins (Basel) 2, 2490-2518 (2010).

Davies, J.A. & Fisher, C.E. Genes and proteins in renal development. Exp Nephrol 10, 102-113 (2002).

Mishra, J. et al. Identification of neutrophil gelatinase-associated lipocalin as a novel early urinary biomarker for ischemic renal injury. J Am Soc Nephrol 14, 2534-2543 (2003).

Vanmassenhove, J., Vanholder, R., Nagler, E. & Van Biesen, W. Urinary and serum biomarkers for the diagnosis of acute kidney injury: an in-depth review of the literature. Nephrol Dial Transplant 28, 254-273 (2013).

Bonventre, J.V. Kidney injury molecule-1 (KIM-1): a urinary biomarker and much more. Nephrol Dial Transplant 24, 3265-3268 (2009).

Wallin, A., Zhang, G., Jones, T.W., Jaken, S. & Stevens, J.L. Mechanism of the nephrogenic repair response. Studies on proliferation and vimentin expression after 35S-1,2-dichlorovinyl-L-cysteine nephrotoxicity in vivo and in cultured proximal tubule epithelial cells. Lab Invest 66, 474-484 (1992).

Weiland, C., Ahr, H.J., Vohr, H.W. & Ellinger-Ziegelbauer, H. Characterization of primary rat proximal tubular cells by gene expression analysis. Toxicol In Vitro 21, 466-491 (2007).

Chabardes-Garonne, D. et al. A panoramic view of gene expression in the human kidney. Proc Natl Acad Sci U S A 100, 13710-13715 (2003).

Simon, D.B. et al. Gitelman's variant of Bartter's syndrome, inherited hypokalaemic alkalosis, is caused by mutations in the thiazide-sensitive Na—Cl cotransporter. Nat Genet 12, 24-30 (1996).

Carota, I. et al. Localization and functional characterization of the human NKCC2 isoforms. Acta Physiol (Oxf) 199, 327-338 (2010).

Vyletal, P., Bleyer, A.J. & Kmoch, S. Uromodulin biology and pathophysiology—an update. Kidney Blood Press Res 33, 456-475 (2010).

Berndt, W.O. The role of transport in chemical nephrotoxicity. Toxicol Pathol 26, 52-57 (1998).

Muller, F. & Fromm, M.F. Transporter-mediated drug-drug interactions. Pharmacogenomics 12, 1017-1037 (2011).

Yang, L. et al. Aristolochic acid nephropathy: variation in presentation and prognosis. Nephrol Dial Transplant 27, 292-298 (2012).

Cortes, C. & Vapnik, V. Support-vector networks. Machine Learning 20, 273-297 (1995).

Ekins, S. Progress in computational toxicology. J Pharmacol Toxicol Methods 69, 115-140 (2014).

Omer, A., Singh, P., Yadav, N.K. & Singh, R.K. An overview of data mining algorithms in drug induced toxicity prediction. Mini Rev Med Chem 14, 345-354 (2014).

Zhang, J.H., Chung, T.D. & Oldenburg, K.R. A Simple Statistical Parameter for Use in Evaluation and Validation of High Throughput Screening Assays. J Biomol Screen 4, 67-73 (1999).

Ritz, C. & Streibig, R. Bioassay analysis using R. J. Stat. Software 12, 1-22 (2005).

Hastie, T., Tibshirani, R. & Friedman, J. (eds.) The Elements of Statistical Learning: Data Mining, Inference, and Prediction, Edn. 2nd (Springer Science +Business Media LLC, Philadelphia, PA, USA; 2009).

Yokote S. et al., De novo kidney regeneration with stem cells, J. Biomed. Biotechnol. Epub Nov. 26, 2012, Review. Abstract; final paragraph of "Discussion"; p. 1348-1349.

Song B et al., The directed differentiation of human iPS cells into kidney podocytes. PLoS One. 2012; 7(9):e46453. Epub Sep. 28, 2012; Abstract, p. 5.

Puri MC and Nagy A. Concise review: Embryonic stem cells versus induced pluripotent stem cells:the game is on. Stem Cells. Jan. 2012;30(1):10-4. Review. Abstract, p. 11-13.

Kurosawa H. Application of Rho-associated protein kinase (ROCK) inhibitor to human pluripotent stem cells. J. Biosci. Bioeng. Dec. 2012; 114(6):577-81. Epub Aug. 13, 2012. Review.

Shin-Ichi Mae et al. "Monitoring and robust induction of nephrogenic intermediate mesoderm from human pluripotent stem cells" Nature Comm., vol. 4, Jan. 22, 2013, p. 1367.

Zay Yar Oo et al. "The performance of primary human renal cells in hollow fiber bioreactors . . ." Biomaterials, Elsevier Science Pub. BV., vol. 32, No. 34, Aug. 10, 2011.

Toshikazu A. et al. "Efficient and Rapid Induction of Human . . . ", PLoS One, vol. 9, No. 1, Jan. 15, 2014, p. e84881.

Extended European Search Report issued in EP 14859928.5 dated Mar. 30, 2017. 10 pages.

Extended European Search Report issued in EP 18192446.5 dated Nov. 26, 2018. 13 pages.

Regeneration and experimental orthotopic transplantation of a bioengineered kidney, by J J Song, J P Guyette, S E Gilpin, G Gonzalez, J P Vacanti & H C Ott Technical Report; Nature Medicine vol. 19, pp. 646-651 (2013).

PSC-Derived Human Microglia-like Cells to Study Neurological Diseases, by E M Abud, R N Ramirez, E S Martinez, M J Carson, W W Poon, M Blurton-Jones; NeuroResource; Neuron 94, 278-293, Apr. 19, 2017.

Assessment of stem cell differentiation based on genome-wide expression profiles, by Godoy P, Schmidt-Heck W, Hellwig B, Nell P, Feuerborn D, Rahnenführer J, Kattler K, Walter J, Blüthgen N, Hengstler JG; Philosophical transactions of the Royal Society of London. Series B, Biological sciences; 2018.

(56) References Cited

OTHER PUBLICATIONS

Mechanosensitive Hair Cell-like Cells from Embryonic and Induced Pluripotent Stem Cells, by K Oshima, K Shin, M Diensthuber, A W. Peng, A J. Ricci, and S Heller; Cell 141, pp. 704-716, May 14, 2010.

* cited by examiner

SEQUENCE LISTING

<160> NUMBER OF SEQ ID NOS: 88

<210> SEQ ID NO 1
<211> LENGTH: 20

```
<212> TYPE: DNA
<213> ORGANISM: artificial
<220> FEATURE:
<223> OTHER INFORMATION: synthetic DNA primer

<400> SEQUENCE: 1
aagctcttct ggagggcagt                                        20

<210> SEQ ID NO 2
<211> LENGTH: 23
<212> TYPE: DNA
<213> ORGANISM: artificial
<220> FEATURE:
<223> OTHER INFORMATION: synthetic DNA primer

<400> SEQUENCE: 2
caccttcacg ttgtcctgga ccg                                    23

<210> SEQ ID NO 3
<211> LENGTH: 19
<212> TYPE: DNA
<213> ORGANISM: artificial
<220> FEATURE:
<223> OTHER INFORMATION: synthetic DNA primer

<400> SEQUENCE: 3
gacgctggga gccttcttg                                         19

<210> SEQ ID NO 4
<211> LENGTH: 18
<212> TYPE: DNA
<213> ORGANISM: artificial
<220> FEATURE:
<223> OTHER INFORMATION: synthetic DNA primer

<400> SEQUENCE: 4
gctggttgtc ggcgaagt                                          18

<210> SEQ ID NO 5
<211> LENGTH: 19
<212> TYPE: DNA
<213> ORGANISM: artificial
<220> FEATURE:
<223> OTHER INFORMATION: synthetic DNA primer

<400> SEQUENCE: 5
gctgacccgc catcgccat                                         19

<210> SEQ ID NO 6
<211> LENGTH: 20
<212> TYPE: DNA
<213> ORGANISM: artificial
<220> FEATURE:
<223> OTHER INFORMATION: synthetic DNA primer

<400> SEQUENCE: 6
accaactgcc accggtcctg                                        20

<210> SEQ ID NO 7
<211> LENGTH: 25
<212> TYPE: DNA
<213> ORGANISM: artificial
<220> FEATURE:
<223> OTHER INFORMATION: synthetic DNA primer

<400> SEQUENCE: 7
```
cacacaccgt tcctggatct cctct                                           25

<210> SEQ ID NO 8
<211> LENGTH: 22
<212> TYPE: DNA
<213> ORGANISM: artificial
<220> FEATURE:
<223> OTHER INFORMATION: synthetic DNA primer

<400> SEQUENCE: 8
gctccaacag gcgaaggtca ct                                              22

<210> SEQ ID NO 9
<211> LENGTH: 24
<212> TYPE: DNA
<213> ORGANISM: artificial
<220> FEATURE:
<223> OTHER INFORMATION: synthetic DNA primer

<400> SEQUENCE: 9
agtcctcaaa gagttgggca taaa                                            24

<210> SEQ ID NO 10
<211> LENGTH: 19
<212> TYPE: DNA
<213> ORGANISM: artificial
<220> FEATURE:
<223> OTHER INFORMATION: synthetic DNA primer

<400> SEQUENCE: 10
acggttccaa cagcaatgg                                                  19

<210> SEQ ID NO 11
<211> LENGTH: 20
<212> TYPE: DNA
<213> ORGANISM: artificial
<220> FEATURE:
<223> OTHER INFORMATION: synthetic DNA primer

<400> SEQUENCE: 11
gaggaccagg actttgactt                                                 20

<210> SEQ ID NO 12
<211> LENGTH: 20
<212> TYPE: DNA
<213> ORGANISM: artificial
<220> FEATURE:
<223> OTHER INFORMATION: synthetic DNA primer

<400> SEQUENCE: 12
agataccggg ggacactcat                                                 20

<210> SEQ ID NO 13
<211> LENGTH: 24
<212> TYPE: DNA
<213> ORGANISM: artificial
<220> FEATURE:
<223> OTHER INFORMATION: synthetic DNA primer

<400> SEQUENCE: 13
accccttcat tgacctcaac taca                                            24

<210> SEQ ID NO 14
<211> LENGTH: 20
<212> TYPE: DNA
<213> ORGANISM: artificial

```
<220> FEATURE:
<223> OTHER INFORMATION: synthetic DNA primer

<400> SEQUENCE: 14
cttgacggtg ccatggaatt                                              20

<210> SEQ ID NO 15
<211> LENGTH: 22
<212> TYPE: DNA
<213> ORGANISM: artificial
<220> FEATURE:
<223> OTHER INFORMATION: synthetic DNA primer

<400> SEQUENCE: 15
acttgggtct gggctatgaa ac                                           22

<210> SEQ ID NO 16
<211> LENGTH: 22
<212> TYPE: DNA
<213> ORGANISM: artificial
<220> FEATURE:
<223> OTHER INFORMATION: synthetic DNA primer

<400> SEQUENCE: 16
tcgtacgttg tctcagctgc at                                           22

<210> SEQ ID NO 17
<211> LENGTH: 24
<212> TYPE: DNA
<213> ORGANISM: artificial
<220> FEATURE:
<223> OTHER INFORMATION: synthetic DNA primer

<400> SEQUENCE: 17
tgagcccaga agtgagagca gttg                                         24

<210> SEQ ID NO 18
<211> LENGTH: 23
<212> TYPE: DNA
<213> ORGANISM: artificial
<220> FEATURE:
<223> OTHER INFORMATION: synthetic DNA primer

<400> SEQUENCE: 18
atgtccacca gctcagagag ggt                                          23

<210> SEQ ID NO 19
<211> LENGTH: 24
<212> TYPE: DNA
<213> ORGANISM: artificial
<220> FEATURE:
<223> OTHER INFORMATION: synthetic DNA primer

<400> SEQUENCE: 19
ccccagctct tcatcactgt tggc                                         24

<210> SEQ ID NO 20
<211> LENGTH: 22
<212> TYPE: DNA
<213> ORGANISM: artificial
<220> FEATURE:
<223> OTHER INFORMATION: synthetic DNA primer

<400> SEQUENCE: 20
tttggaacac aaggaggggg cc                                           22
```

```
<210> SEQ ID NO 21
<211> LENGTH: 22
<212> TYPE: DNA
<213> ORGANISM: artificial
<220> FEATURE:
<223> OTHER INFORMATION: synthetic DNA primer

<400> SEQUENCE: 21
aaaaagcgct gtccctatac ca                                          22

<210> SEQ ID NO 22
<211> LENGTH: 21
<212> TYPE: DNA
<213> ORGANISM: artificial
<220> FEATURE:
<223> OTHER INFORMATION: synthetic DNA primer

<400> SEQUENCE: 22
tgaggttgag catccgagag a                                           21

<210> SEQ ID NO 23
<211> LENGTH: 20
<212> TYPE: DNA
<213> ORGANISM: artificial
<220> FEATURE:
<223> OTHER INFORMATION: synthetic DNA primer

<400> SEQUENCE: 23
tggctgcagg acatgacaac                                             20

<210> SEQ ID NO 24
<211> LENGTH: 21
<212> TYPE: DNA
<213> ORGANISM: artificial
<220> FEATURE:
<223> OTHER INFORMATION: synthetic DNA primer

<400> SEQUENCE: 24
tgaggtgccc atgctacatt t                                           21

<210> SEQ ID NO 25
<211> LENGTH: 21
<212> TYPE: DNA
<213> ORGANISM: artificial
<220> FEATURE:
<223> OTHER INFORMATION: synthetic DNA primer

<400> SEQUENCE: 25
ttggcagcct tcctgatttc t                                           21

<210> SEQ ID NO 26
<211> LENGTH: 22
<212> TYPE: DNA
<213> ORGANISM: artificial
<220> FEATURE:
<223> OTHER INFORMATION: synthetic DNA primer

<400> SEQUENCE: 26
gggtggaaag gtttggagta tg                                          22

<210> SEQ ID NO 27
<211> LENGTH: 20
<212> TYPE: DNA
<213> ORGANISM: artificial
<220> FEATURE:
<223> OTHER INFORMATION: synthetic DNA primer
```

```
<400> SEQUENCE: 27
caggctgatc ccataatgca                                             20

<210> SEQ ID NO 28
<211> LENGTH: 22
<212> TYPE: DNA
<213> ORGANISM: artificial
<220> FEATURE:
<223> OTHER INFORMATION: synthetic DNA primer

<400> SEQUENCE: 28
ctgcctctcc accaacctttt ac                                         22

<210> SEQ ID NO 29
<211> LENGTH: 20
<212> TYPE: DNA
<213> ORGANISM: artificial
<220> FEATURE:
<223> OTHER INFORMATION: synthetic DNA primer

<400> SEQUENCE: 29
tcccatgcct acctcaccttt                                            20

<210> SEQ ID NO 30
<211> LENGTH: 19
<212> TYPE: DNA
<213> ORGANISM: artificial
<220> FEATURE:
<223> OTHER INFORMATION: synthetic DNA primer

<400> SEQUENCE: 30
ttgcagcgac acacgatca                                              19

<210> SEQ ID NO 31
<211> LENGTH: 25
<212> TYPE: DNA
<213> ORGANISM: artificial
<220> FEATURE:
<223> OTHER INFORMATION: synthetic DNA primer

<400> SEQUENCE: 31
gcccttgtta gacagcctca tattt                                       25

<210> SEQ ID NO 32
<211> LENGTH: 18
<212> TYPE: DNA
<213> ORGANISM: artificial
<220> FEATURE:
<223> OTHER INFORMATION: synthetic DNA primer

<400> SEQUENCE: 32
ggacaggcgg tgagcaat                                               18

<210> SEQ ID NO 33
<211> LENGTH: 24
<212> TYPE: DNA
<213> ORGANISM: artificial
<220> FEATURE:
<223> OTHER INFORMATION: synthetic DNA primer

<400> SEQUENCE: 33
agactggttc taacgcctgt aatc                                        24

<210> SEQ ID NO 34
```

```
<211> LENGTH: 21
<212> TYPE: DNA
<213> ORGANISM: artificial
<220> FEATURE:
<223> OTHER INFORMATION: synthetic DNA primer

<400> SEQUENCE: 34
gctctgtggg tggttcattg g                                         21

<210> SEQ ID NO 35
<211> LENGTH: 22
<212> TYPE: DNA
<213> ORGANISM: artificial
<220> FEATURE:
<223> OTHER INFORMATION: synthetic DNA primer

<400> SEQUENCE: 35
tcgcaaaaaa ggaagacaag gt                                        22

<210> SEQ ID NO 36
<211> LENGTH: 22
<212> TYPE: DNA
<213> ORGANISM: artificial
<220> FEATURE:
<223> OTHER INFORMATION: synthetic DNA primer

<400> SEQUENCE: 36
gagtacacac agctgggtgg aa                                        22

<210> SEQ ID NO 37
<211> LENGTH: 23
<212> TYPE: DNA
<213> ORGANISM: artificial
<220> FEATURE:
<223> OTHER INFORMATION: synthetic DNA primer

<400> SEQUENCE: 37
ccaaactgga ggagcgacgg aag                                       23

<210> SEQ ID NO 38
<211> LENGTH: 22
<212> TYPE: DNA
<213> ORGANISM: artificial
<220> FEATURE:
<223> OTHER INFORMATION: synthetic DNA primer

<400> SEQUENCE: 38
cacacacatg cttgaggaag ga                                        22

<210> SEQ ID NO 39
<211> LENGTH: 22
<212> TYPE: DNA
<213> ORGANISM: artificial
<220> FEATURE:
<223> OTHER INFORMATION: synthetic DNA primer

<400> SEQUENCE: 39
cccatacacc agcctggaac gc                                        22

<210> SEQ ID NO 40
<211> LENGTH: 20
<212> TYPE: DNA
<213> ORGANISM: artificial
<220> FEATURE:
<223> OTHER INFORMATION: synthetic DNA primer

<400> SEQUENCE: 40
```
tgggtcggtc tggatggcga                                              20

<210> SEQ ID NO 41
<211> LENGTH: 22
<212> TYPE: DNA
<213> ORGANISM: artificial
<220> FEATURE:
<223> OTHER INFORMATION: synthetic DNA primer

<400> SEQUENCE: 41
caccaagagg tttgaggaca tg                                           22

<210> SEQ ID NO 42
<211> LENGTH: 21
<212> TYPE: DNA
<213> ORGANISM: artificial
<220> FEATURE:
<223> OTHER INFORMATION: synthetic DNA primer

<400> SEQUENCE: 42
gacagtggcc tcatccttga a                                            21

<210> SEQ ID NO 43
<211> LENGTH: 23
<212> TYPE: DNA
<213> ORGANISM: artificial
<220> FEATURE:
<223> OTHER INFORMATION: synthetic DNA primer

<400> SEQUENCE: 43
caaggagctg acttcggaac taa                                          23

<210> SEQ ID NO 44
<211> LENGTH: 20
<212> TYPE: DNA
<213> ORGANISM: artificial
<220> FEATURE:
<223> OTHER INFORMATION: synthetic DNA primer

<400> SEQUENCE: 44
tgcactcagc cgtcgataca                                              20

<210> SEQ ID NO 45
<211> LENGTH: 24
<212> TYPE: DNA
<213> ORGANISM: artificial
<220> FEATURE:
<223> OTHER INFORMATION: synthetic DNA primer

<400> SEQUENCE: 45
tggggagtca tgctcttcat tcgc                                         24

<210> SEQ ID NO 46
<211> LENGTH: 23
<212> TYPE: DNA
<213> ORGANISM: artificial
<220> FEATURE:
<223> OTHER INFORMATION: synthetic DNA primer

<400> SEQUENCE: 46
ccacgaacaa acccgttagt tgc                                          23

<210> SEQ ID NO 47
<211> LENGTH: 21
<212> TYPE: DNA

```
<213> ORGANISM: artificial
<220> FEATURE:
<223> OTHER INFORMATION: synthetic DNA primer

<400> SEQUENCE: 47
tctactcctg gttcttcatt g                                              21

<210> SEQ ID NO 48
<211> LENGTH: 21
<212> TYPE: DNA
<213> ORGANISM: artificial
<220> FEATURE:
<223> OTHER INFORMATION: synthetic DNA primer

<400> SEQUENCE: 48
cggagtacct ccatactcaa t                                              21

<210> SEQ ID NO 49
<211> LENGTH: 20
<212> TYPE: DNA
<213> ORGANISM: artificial
<220> FEATURE:
<223> OTHER INFORMATION: synthetic DNA primer

<400> SEQUENCE: 49
gcccttggac ttgcagaccg                                                20

<210> SEQ ID NO 50
<211> LENGTH: 20
<212> TYPE: DNA
<213> ORGANISM: artificial
<220> FEATURE:
<223> OTHER INFORMATION: synthetic DNA primer

<400> SEQUENCE: 50
acctgtttgc ctgatgactg                                                20

<210> SEQ ID NO 51
<211> LENGTH: 23
<212> TYPE: DNA
<213> ORGANISM: artificial
<220> FEATURE:
<223> OTHER INFORMATION: synthetic DNA primer

<400> SEQUENCE: 51
gctgtacccc acattcatta gga                                            23

<210> SEQ ID NO 52
<211> LENGTH: 21
<212> TYPE: DNA
<213> ORGANISM: artificial
<220> FEATURE:
<223> OTHER INFORMATION: synthetic DNA primer

<400> SEQUENCE: 52
gggagctcaa gccagatgtt a                                              21

<210> SEQ ID NO 53
<211> LENGTH: 23
<212> TYPE: DNA
<213> ORGANISM: artificial
<220> FEATURE:
<223> OTHER INFORMATION: synthetic DNA primer

<400> SEQUENCE: 53
ggaggaagct gacaacaatg aaa                                            23
```

<210> SEQ ID NO 54
<211> LENGTH: 21
<212> TYPE: DNA
<213> ORGANISM: artificial
<220> FEATURE:
<223> OTHER INFORMATION: synthetic DNA primer

<400> SEQUENCE: 54
ggttgcctct cactcggttc t                                         21

<210> SEQ ID NO 55
<211> LENGTH: 19
<212> TYPE: DNA
<213> ORGANISM: artificial
<220> FEATURE:
<223> OTHER INFORMATION: synthetic DNA primer

<400> SEQUENCE: 55
ggtttggccg gaagaatgt                                            19

<210> SEQ ID NO 56
<211> LENGTH: 22
<212> TYPE: DNA
<213> ORGANISM: artificial
<220> FEATURE:
<223> OTHER INFORMATION: synthetic DNA primer

<400> SEQUENCE: 56
ccatgcctac aaggacaaac ag                                        22

<210> SEQ ID NO 57
<211> LENGTH: 21
<212> TYPE: DNA
<213> ORGANISM: artificial
<220> FEATURE:
<223> OTHER INFORMATION: synthetic DNA primer

<400> SEQUENCE: 57
ccctgcagct caccaactac t                                         21

<210> SEQ ID NO 58
<211> LENGTH: 20
<212> TYPE: DNA
<213> ORGANISM: artificial
<220> FEATURE:
<223> OTHER INFORMATION: synthetic DNA primer

<400> SEQUENCE: 58
agatggtccg aaggcactgt                                           20

<210> SEQ ID NO 59
<211> LENGTH: 21
<212> TYPE: DNA
<213> ORGANISM: artificial
<220> FEATURE:
<223> OTHER INFORMATION: synthetic DNA primer

<400> SEQUENCE: 59
cttccaggca tcagagcaca t                                         21

<210> SEQ ID NO 60
<211> LENGTH: 24
<212> TYPE: DNA
<213> ORGANISM: artificial
<220> FEATURE:

<223> OTHER INFORMATION: synthetic DNA primer

<400> SEQUENCE: 60
gtggatgcag atagactcga cttg                                          24

<210> SEQ ID NO 61
<211> LENGTH: 23
<212> TYPE: DNA
<213> ORGANISM: artificial
<220> FEATURE:
<223> OTHER INFORMATION: synthetic DNA primer

<400> SEQUENCE: 61
cagtgggccg agtacattct att                                           23

<210> SEQ ID NO 62
<211> LENGTH: 21
<212> TYPE: DNA
<213> ORGANISM: artificial
<220> FEATURE:
<223> OTHER INFORMATION: synthetic DNA primer

<400> SEQUENCE: 62
tctccgctgg gttgatgtaa g                                             21

<210> SEQ ID NO 63
<211> LENGTH: 21
<212> TYPE: DNA
<213> ORGANISM: artificial
<220> FEATURE:
<223> OTHER INFORMATION: synthetic DNA primer

<400> SEQUENCE: 63
acctaccctg ccagagacca t                                             21

<210> SEQ ID NO 64
<211> LENGTH: 23
<212> TYPE: DNA
<213> ORGANISM: artificial
<220> FEATURE:
<223> OTHER INFORMATION: synthetic DNA primer

<400> SEQUENCE: 64
agatcctcac actttgccca gtt                                           23

<210> SEQ ID NO 65
<211> LENGTH: 23
<212> TYPE: DNA
<213> ORGANISM: artificial
<220> FEATURE:
<223> OTHER INFORMATION: synthetic DNA primer

<400> SEQUENCE: 65
gtgcatgcct agtcctagct gat                                           23

<210> SEQ ID NO 66
<211> LENGTH: 23
<212> TYPE: DNA
<213> ORGANISM: artificial
<220> FEATURE:
<223> OTHER INFORMATION: synthetic DNA primer

<400> SEQUENCE: 66
ctcactctag gctcaagcaa tcc                                           23

```
<210> SEQ ID NO 67
<211> LENGTH: 20
<212> TYPE: DNA
<213> ORGANISM: artificial
<220> FEATURE:
<223> OTHER INFORMATION: synthetic DNA primer

<400> SEQUENCE: 67
acgcctgatt cccgagttct                                               20

<210> SEQ ID NO 68
<211> LENGTH: 21
<212> TYPE: DNA
<213> ORGANISM: artificial
<220> FEATURE:
<223> OTHER INFORMATION: synthetic DNA primer

<400> SEQUENCE: 68
agaacagcac aatggcgaag t                                             21

<210> SEQ ID NO 69
<211> LENGTH: 22
<212> TYPE: DNA
<213> ORGANISM: artificial
<220> FEATURE:
<223> OTHER INFORMATION: synthetic DNA primer

<400> SEQUENCE: 69
aggaaaggga gaacaacgag aa                                            22

<210> SEQ ID NO 70
<211> LENGTH: 21
<212> TYPE: DNA
<213> ORGANISM: artificial
<220> FEATURE:
<223> OTHER INFORMATION: synthetic DNA primer

<400> SEQUENCE: 70
gagctgccta acaccgactt g                                             21

<210> SEQ ID NO 71
<211> LENGTH: 21
<212> TYPE: DNA
<213> ORGANISM: artificial
<220> FEATURE:
<223> OTHER INFORMATION: synthetic DNA primer

<400> SEQUENCE: 71
ctgggtcaca ggctactttg c                                             21

<210> SEQ ID NO 72
<211> LENGTH: 21
<212> TYPE: DNA
<213> ORGANISM: artificial
<220> FEATURE:
<223> OTHER INFORMATION: synthetic DNA primer

<400> SEQUENCE: 72
gccctctcaa tgctgatcac a                                             21

<210> SEQ ID NO 73
<211> LENGTH: 20
<212> TYPE: DNA
<213> ORGANISM: artificial
<220> FEATURE:
<223> OTHER INFORMATION: synthetic DNA primer
```

```
<400> SEQUENCE: 73
tcatcaccaa ctgggacgac                                               20

<210> SEQ ID NO 74
<211> LENGTH: 20
<212> TYPE: DNA
<213> ORGANISM: artificial
<220> FEATURE:
<223> OTHER INFORMATION: synthetic DNA primer

<400> SEQUENCE: 74
atgctcttca ggggcaacac                                               20

<210> SEQ ID NO 75
<211> LENGTH: 19
<212> TYPE: DNA
<213> ORGANISM: artificial
<220> FEATURE:
<223> OTHER INFORMATION: synthetic DNA primer

<400> SEQUENCE: 75
atcccatcac ccacagcaa                                                19

<210> SEQ ID NO 76
<211> LENGTH: 17
<212> TYPE: DNA
<213> ORGANISM: artificial
<220> FEATURE:
<223> OTHER INFORMATION: synthetic DNA primer

<400> SEQUENCE: 76
gtcggcatcg cggtttt                                                  17

<210> SEQ ID NO 77
<211> LENGTH: 18
<212> TYPE: DNA
<213> ORGANISM: artificial
<220> FEATURE:
<223> OTHER INFORMATION: synthetic DNA primer

<400> SEQUENCE: 77
gggtccacag cgcatgat                                                 18

<210> SEQ ID NO 78
<211> LENGTH: 24
<212> TYPE: DNA
<213> ORGANISM: artificial
<220> FEATURE:
<223> OTHER INFORMATION: synthetic DNA primer

<400> SEQUENCE: 78
tttaagagct gtgatctcct cgtt                                          24

<210> SEQ ID NO 79
<211> LENGTH: 24
<212> TYPE: DNA
<213> ORGANISM: artificial
<220> FEATURE:
<223> OTHER INFORMATION: synthetic DNA primer

<400> SEQUENCE: 79
tggcttcagg acaccagaca tcag                                          24

<210> SEQ ID NO 80
<211> LENGTH: 23
```

```
<212> TYPE: DNA
<213> ORGANISM: artificial
<220> FEATURE:
<223> OTHER INFORMATION: synthetic DNA primer

<400> SEQUENCE: 80
agcacctgcc caaggaaag acg                                          23

<210> SEQ ID NO 81
<211> LENGTH: 20
<212> TYPE: DNA
<213> ORGANISM: artificial
<220> FEATURE:
<223> OTHER INFORMATION: synthetic DNA primer

<400> SEQUENCE: 81
acctgaggga aactaatctg                                             20

<210> SEQ ID NO 82
<211> LENGTH: 20
<212> TYPE: DNA
<213> ORGANISM: artificial
<220> FEATURE:
<223> OTHER INFORMATION: synthetic DNA primer

<400> SEQUENCE: 82
cgttgataac ctgtccatct                                             20

<210> SEQ ID NO 83
<211> LENGTH: 20
<212> TYPE: DNA
<213> ORGANISM: artificial
<220> FEATURE:
<223> OTHER INFORMATION: synthetic DNA primer

<400> SEQUENCE: 83
ggaaattctc gtgtcccaga                                             20

<210> SEQ ID NO 84
<211> LENGTH: 21
<212> TYPE: DNA
<213> ORGANISM: artificial
<220> FEATURE:
<223> OTHER INFORMATION: synthetic DNA primer

<400> SEQUENCE: 84
tgacacagag tgaccagcgt a                                           21

<210> SEQ ID NO 85
<211> LENGTH: 25
<212> TYPE: DNA
<213> ORGANISM: artificial
<220> FEATURE:
<223> OTHER INFORMATION: synthetic DNA primer

<400> SEQUENCE: 85
aacagcaaca gcaagaaata aatca                                       25

<210> SEQ ID NO 86
<211> LENGTH: 24
<212> TYPE: DNA
<213> ORGANISM: artificial
<220> FEATURE:
<223> OTHER INFORMATION: synthetic DNA primer

<400> SEQUENCE: 86
```

```
gacctcggga atgttagaca agat                                            24

<210> SEQ ID NO 87
<211> LENGTH: 20
<212> TYPE: DNA
<213> ORGANISM: artificial
<220> FEATURE:
<223> OTHER INFORMATION: synthetic DNA primer

<400> SEQUENCE: 87
gagaggattt gtccgctcag                                                 20

<210> SEQ ID NO 88
<211> LENGTH: 20
<212> TYPE: DNA
<213> ORGANISM: artificial
<220> FEATURE:
<223> OTHER INFORMATION: synthetic DNA primer

<400> SEQUENCE: 88
aggcctcaga aatccagctt                                                 20
```

METHOD FOR DIFFERENTIATING INDUCED PLURIPOTENT STEM CELLS INTO RENAL PROXIMAL TUBULAR CELL-LIKE CELLS

CROSS-REFERENCE TO RELATED APPLICATIONS

This patent application is a U.S. National Phase Application under 35 U.S.C. § 371 of International Application No. PCT/SG2014/000529, filed on Nov. 11, 2014, entitled METHOD FOR DIFFERENTIATING INDUCED PLURIPOTENT STEM CELLS INTO RENAL PROXIMAL TUBULAR CELL-LIKE CELLS, which claims benefit of, and priority from, Singapore provisional application No. 201308341-5, filed on Nov. 11, 2013, the contents of which were incorporated by reference.

INCORPORATION BY REFERENCE

This application incorporates by reference the material (i.e., Sequence Listing) in the ASCII text file named Sequence_Listing.txt, created on May 4, 2016 (modified on May 4, 2016), having a file size of 16,506 bytes.

FIELD OF THE INVENTION

The present invention relates to methods for producing renal proximal tubular cell-like cells, by differentiation of induced pluripotent stem cells.

BACKGROUND

Renal epithelial cells may be useful in treating renal disorders. This includes applications inbio-artificial kidney devices to replace or compensate for lost organ functions. Thus, a sufficient supply of renal epithelial cells is required. Of particular interest are renal proximal tubular cells (PTC), which perform various renal functions.

Renal proximal tubular cells function in drug transport and metabolism, and thus are also of particular interest for in vitro nephrotoxicology. This cell type is a major target of drug-induced toxicity in the kidney. Many widely used marketed drugs, including anti-cancer drugs, antibiotics, immunospressants and radiocontrast agents, tend to be nephrotoxic and thus may injure proximal tubular cells in the kidney. Drug-induced nephrotoxicity is a major cause for acute kidney injury (AKI).

Nonetheless, the prediction of nephrotoxicity during drug development remains difficult. Typically, compound nephrotoxicity is only detected during the later stages of drug development. Pre-clinical animal models have limited predictive success; the development of in vitro models for assaying nephrotoxicity that demonstrate strong predictivity has been challenging. Most existing in vitro assays systems have been based on established cell lines. Primary renal proximal tubular cells are only available in limited amounts and can be affected by inter-donor variability and functional changes during in vitro cultivation and passaging.

Previous technology described a method for differentiation of human embryonic stem cells (hESCs) into cells expressing aquaporin (AQP)-1. In the kidney, AQP-1 is specifically expressed in proximal tubular cells. About 30% of the hESC-derived cells expressed AQP-1, and further analyses showed that hESC-derived cells were similar to human primary renal proximal tubular cells (HPTC) cultivated in vitro with respect to gene and protein expression patterns and morphological and functional features. hESC-based technologies are affected by ethical and related legal issues, which may compromise commercialization. Also, the relatively low rate (30%) of hESC-derived HPTC-like cells is a problem, and purification procedures would be required in order for such HPTC-like cells to be useful in any practical applications. Further, hESC-derived cells express some major drug transporters like the organic anion transporter (OAT)3 at very low levels, which may compromise application of such cells in in vitro nephrotoxiclogy.

SUMMARY

The present invention relates to the use of induced pluripotent stem cells (iPSCs), including human iPSCs (hiPSCs) to produce renal proximal tubular cell (PTC)-like cells, including human primary renal proximal tubular cell (HPTC)-like cells.

In the population of differentiated cells produced by the method, in some embodiments about 90% or greater of the cells may be differentiated to be PTC-like cells.

Such high purity of differentiated cell type means that the cell population may be used directly in some applications without further processing, harvesting, purification or sorting.

Thus, the method may provide a rapid, one-step protocol for producing a population of PTC-like cells, including HPTC-like cells, which can then be used in various applications, such as in vitro toxicology assays to predict PTC-toxicity, including during drug development studies. Such in vitro studies may use machine learning algorithms, and thus may obtain highly accurate results regarding prediction of PTC-toxicity.

In one aspect, the invention provides a method of differentiating an induced pluripotent stem cell (iPSC) into a renal proximal tubular cell (PTC)-like cell, the method comprising: culturing an undifferentiated iPSC in a renal epithelial cell culture medium in the presence of one or more extracellular matrix (ECM) molecules, bone morphogenic protein 2 (BMP2) and bone morphogenic protein 7 (BMP7), for a period of from about 8 to about 10 days, under conditions sufficient to induce differentiation of the iPSC into a PTC-like cell.

The iPSC may be any type of iPSC, including a mammalian iPSC or a human iPSC.

The iPSC may be initially seeded in the presence of ROCK inhibitor and in the absence of BMP2 and BMP7, prior to the culturing. The iPSC may be seeded at an initial density of about 5 000 to about 10 000 viable cells/cm$^2$, or about 8 000 viable cells/cm$^2$.

The one or more ECM molecule may, in some embodiments, comprise Matrigel matrix, including growth factor reduced Matrigel matrix.

The renal epithelial cell culture medium may comprise renal epithelial cell growth medium.

The BMP2 and the BMP7 may be added to the renal epithelial cell culture medium about 12 to about 24 hours after initial seeding of the iPSC. The BMP2 may be present during the culturing in a concentration from about 1 ng/ml to about 25 ng/ml, or from about 2.5 ng/ml to about 15 ng/ml. The BMP7 may be present during the culturing in a concentration from about 0.25 ng/ml to about 10 ng/ml, or about 1 ng/ml to about 5 ng/ml.

In some embodiments, the iPSC is a human iPSC and the method comprises seeding the undifferentiated iPSC at a density of about 8 000 viable cells/cm$^2$, in renal epithelial cell growth medium that is free from BMP2 and BMP7 and which comprises about 5 µM to about 15 µM ROCK inhibitor, for about 12 hours to about 24 hours in order to allow the undifferentiated iPSC to attach to a culture support coated with growth factor reduced Matrigel matrix; exchanging the renal epithelial cell growth medium for fresh renal epithelial cell growth medium that is free from ROCK inhibitor and which comprises from about 2.5 ng/ml to about 15 ng/ml BMP2 and from about 1 ng/ml to about 5 ng/ml BMP7; culturing the iPSC in the renal epithelial cell growth medium comprising BMP2 and BMP7 for a period of from about 8 to about 10 days, at a temperature of about 37° C. and under about 5% $CO_2$, under conditions sufficient to induce differentiation of the iPSC into a PTC-like cell.

In another aspect, the invention provides a population of PTC-like cells differentiated from a population of induced pluripotent stem cells (iPSCs) seeded at a density of about 5 000 to about 10 000 viable cells/$cm^2$, in renal epithelial cell culture medium in the presence of one or more extracellular matrix molecule, bone morphogenic protein 2, and bone morphogenic protein 7, for a period of from about 7 to about 10 days.

The population of cells may be prepared in accordance with a method of the invention.

In some embodiments, in the population of cells, about 90% or greater of the cells express AQP1, PEPT1, OAT3 and GLUT1.

In some embodiments, the population of cells may be contained in a hollow fibre bioreactor of a bioartificial kidney device, a hydrogel, or a bioengineered graft.

Thus, in another aspect, the invention provides a bioengineered tissue graft comprising a matrix seeded with the population of cells of the invention. The matrix may be a decellularized matrix or may be a 3D renal matrix.

In another aspect, the invention provides an in vitro method for screening nephrotoxicity of a compound, the method comprising: contacting a test compound with a test population of cells of the invention; and determining the effect of the test compound in comparison to a control population of cells that has not been contacted with the test compound.

The test population may be assessed with respect to the effect of the test compound on cell viability, cell number, expression of a marker gene, cell morphology, arrangement of a cytoskeletal component, translocation of cellular factor, ATP depletion, mitochondrial damage, glutathione (GSH) depletion, membrane damage, generation of reactive oxygen species or DNA damage.

In some embodiments of the method, the test population of cells may be prepared according to a method of the invention, and the contacting may be performed on the test population after about 8 to about 10 days of differentiating without harvesting prior to the contacting.

In another aspect, the invention provides a method of preparing a bioartificial kidney device, the method comprising seeding the device with a population of cells of the invention.

In another aspect, the invention provides a method of treating a renal related disorder in a subject comprising externally connecting a bioartificial kidney device containing a population of cells of the invention.

In another aspect, the invention provides use a bioartificial kidney device containing a population of cells of the invention for treating a renal related disorder in a subject in need thereof.

In another aspect, the invention provides use of a population of cells of the invention for the manufacture of a bioartificial kidney device for treating a renal related disorder in a subject in need thereof.

In another aspect, the invention provides a bioartificial kidney device containing a population of cells of the invention for use in the treatment of a renal related disorder in a subject in need thereof.

In another aspect, the invention provides a method of treating a renal related disorder in a subject in need thereof, the method comprising implanting an effective amount of a population of cells of the invention, or the bioengineered tissue graft of the invention, in the subject at a site where PTC-like cells are required.

In another aspect, the invention provides use of an effective amount of a population of cells of the invention, or the bioengineered tissue graft of the invention, for treating a renal related disorder in a subject in need thereof.

In another aspect, the invention provides use of an effective amount of a population of cells for the manufacture of a bioengineered tissue graft of the invention, for treating a renal related disorder in a subject in need thereof.

In another aspect, the invention provides an effective amount of a population of cells of the invention, or a bioengineered tissue graft of the invention, for use in the treatment of a renal related disorder in a subject in need thereof.

In some embodiments of the methods and uses, the renal related disorder comprises acute kidney injury, chronic kidney disease, end stage renal disease, nephropathy, diabetic nephropathy, nephrosis, Bright's disease, renal insufficiency, glomerulitis, glomerulosclerosis, or nephritis.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The figures, which illustrate, by way of example only, embodiments of the present invention, are as follows.

DETAILED DESCRIPTION

Figure 1:
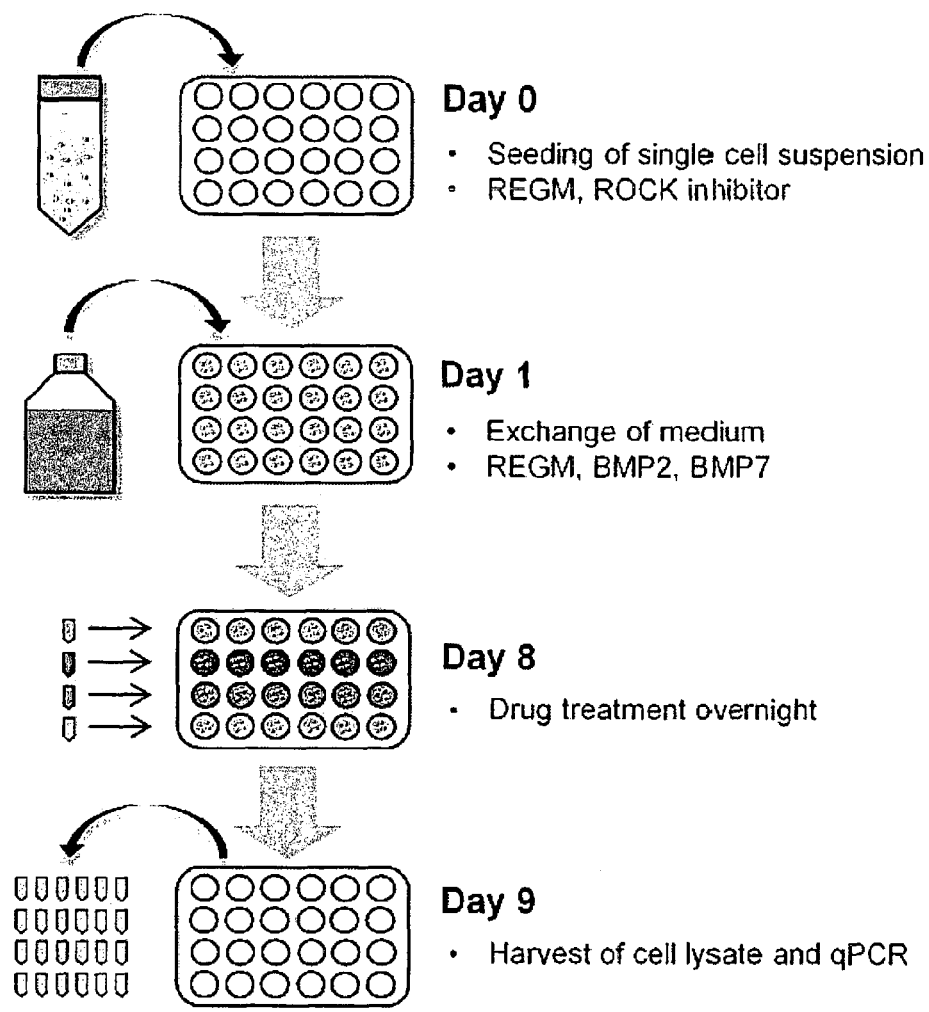
FIG. 1. Flowchart depicting an embodiment of the method for the differentiation procedure with subsequent drug testing.

The present invention relates to a differentiation method for differentiating iPSCs into renal proximal tubular cell (PTC)-like cells, including differentiating hiPSCs into HPTC-like cells, cell populations made by the differentiation method and methods of using and uses of such cell populations.

Previously, a variety of protocols have been developed for the differentiation of human or murine embryonic (ESC) or induced pluripotent stem cells (iPSC) into the renal lineage. Some of these previous approaches were designed to recapitulate embryonic kidney development and involved indirect differentiation having multiple steps to mimic the different stages. Such protocols generated embryonic kidney precursors and resulted typically in a mix of different renal cell types. Although the results are interesting with respect to applications in regenerative medicine, the applicability for drug screening is limited. No drug toxicity applications based on these approaches have been established yet.

In addition, an hESC-based approach has been previously described (Narayanan et al., Kidney Int., 2013), which is not a multistep protocol. HPTC-like cells obtained by the method of Narayanan et al. have been used for in vitro toxicology assays (Li et al., Mol. Pharm., 2014).

Although human embryonic stem cells (hESCs) have previously been differentiated into cells that express AQP-1, the use of embryonic stem cells can be controversial. Human iPSCs, however, are not affected by the same ethical and legal issues as faced by hESCs. Thus, potential applications for renal epithelial cells derived from hiPSCs include drug screening and in vitro toxicology.

Prior to the present invention, there has not been a reliable, well-characterized method for obtaining PTC-like cells from iPSCs. These methods and cells have now been obtained, as described herein. The PTC-like cells of the present invention have been found to have many features of PTCs and may be useful in applications where PTCs may be used, including nephrotoxicity assays and in therapeutic applications for renal deficiencies and disorders, including in bioartificial kidney devices.

The method involves direct differentiation of an iPSC into a PTC-like cell, meaning that differentiation occurs into the PTC-like cell without the formation of embryoid bodies (EBs). An EB is an aggregate of cells that can facilitate differentiation comparable to an embryo and thus can contains cells from all three germ layers, the ectoderm, meosderm and endoderm. In indirect differentiation, ES cells are first aggregated to form EBs and then the EBs are exposed to conditions to promote differentiation into renal progenitor cells. Since the formation of EBs leads to the formation of multiple cell types, indirect differentiation using EBs results in a heterogeneous population of differentiated cells and a low yield of renal progenitor cells. Thus, the present method allows for a relatively uniform cellular environment and a more homogeneous population of differentiated cells, and thus is likely to provide a higher yield of PTC-like cells than methods involving the formation of EBs.

Briefly, a PTC-like cell obtained from the present differentiation method is a cell that is directly differentiated from an iPSC, and that expresses one or more renal-specific or PTC-specific cellular markers. Thus, the PTC-like cell obtained in the method is "derived from" or "differentiated from" an iPSC. A renal-specific or PTC-specific cellular marker includes a cellular gene or protein expressed in PTCs, including HPTCs, and which is not expressed or is expressed to a lesser extent in iPSCs, including human iPSCs. Such a marker may be used as indication that a particular cell has differentiated from an iPSC cell to become a PTC-like cell. Such markers include, for example VIT D3, SLC34A1, NBC1, $Na^+/K^+$ ATPase, KSP-CAD, AQP1, GGT, CD13, OAT1, MEG, OAT3, OCT2, OCTN2, PEPT1, GLUT1, GLUT5, SGLT1, SGLT2, URO-10 or ZO-1 (see Table 1 for full gene and protein names). In some embodiments, a PTC-like cell derived from iPSC in the method may express OAT3. In some embodiments, a PTC-like cell derived from iPSC in the method may express AQP1, PEPT1, OAT3 and GLUT1. In some embodiments, a PTC-like cell derived from iPSC in the method may express $Na^+/K^+$ ATPase, AQP1, PEPT1, OAT3. SGLT2, URO10, ZO-1 and GLUT1. Baso-lateral drug uptake transporters OAT1, OAT3 and OCT2 may be expressed in the iPSC-derived PTC-like cell. The major phosphate uptake transporter SLC34A1 may be expressed in the iPSC-derived PTC-like cell.

Thus, a method of differentiating iPSCs into PTC-like cells is provided. The method as described herein is a direct differentiation method and may be used as a rapid, one-step protocol in some embodiments. That is, for some applications it is possible to use the differentiated cell population immediately upon completion of the differentiation period, for example in in vitro toxicity assays, without the need for further cell harvesting or cell sorting.

Thus, the method involves differentiating an induced pluripotent stem cell (iPSC) into a renal proximal tubular cell (PTC)-like cell. Briefly, the method comprises culturing an undifferentiated iPSC in renal epithelial cell culture medium in the presence of bone morphogenic protein 2 and bone morphogenic protein 7, for a period of from about 8 days to about 10 days, under conditions sufficient to induce differentiation of the iPSC into a PTC-like cell.

As used herein, the term "cell", including when used in the context of an iPSC or a PTC-like cell, is intended to refer to a single cell as well as a plurality or population of cells, where context allows. Similarly, the term "cells" is also intended to refer to a single cell, where context allows. The cell may be a cell grown in batch culture or in tissue culture plates, and may be in suspension or may be attached to a culture support surface.

As used herein, an iPSC is a pluripotent stem cell that has been induced to a pluripotent state from a non-pluripotent originator cell, for example a partially or fully differentiated cell that can be induced to become pluripotent by exposure to appropriate conditions and transcription factors or other protein factors that regulate gene expression profiles in pluripotent cells, for example Sox2, Oct4, c-Myc and Klf4. Methods of inducing pluripotency are known, for example as described in Takahashi and Yamanaka, Cell 126 (2006), 663-676. Thus, the iPSC is a pluripotent cell that has been derived from a non-pluripotent originator cell and is not an embryonic stem cell.

The induced pluripotent stem cell, or iPSC, may be any type of iPSC, including an animal iPSC, including a mammalian iPSC, including a human iPSC. The iPSC may be from an established iPSC culture or source, for example a commercially available iPSC source. Human iPSC may be derived from a normal subject or from a patient. The patient may be affected by a renal disease or may be sensitive to a drug effect, including an adverse drug effect. Human iPSC may be also derived from a relative of such a patient. The iPSC may be induced to be pluripotent from a non-pluripotent cell specifically for use in the methods described herein, including shortly before or immediately before use, or may be stored or maintained in culture for a period of time prior to use in the differentiation methods described herein.

Prior to seeding for differentiation, the iPSC may be maintained or propagated in an undifferentiated state. Generally, methods of culturing iPSCs to maintain the cells in an undifferentiated state are known and thus the iPSC may be maintained in an undifferentiated state using known methods for iPSCs. The iPSC may be maintained in a suitable medium that does not induce differentiation, for example in mTesR1 medium. Generally, mTeSR1 is a defined medium that can be used for feeder-free culturing of hESC and iPSC. In some embodiments, mTeSR1 contains bovine serum albumin, rh bFGF, rh TGFβ, lithium chloride, pipecolic acid and GABA. Although the mTeSR1 defined medium may be commercially available, this medium is known and protocols are available that allow a skilled person to readily prepare mTeSR1 using routine laboratory methods. (Ludwig et al., *Nature Methods,* 2006a, 3:637-646; Ludwig et al., *Nature Biotechnology,* 2006b, 24:185-187.) Other media that also do not induce differentiation of stem cells may be used to maintain or propagate the iPSC prior to use in the differentiation-method.

In order to differentiate the iPSC, the undifferentiated iPSC is seeded onto a culture surface of an appropriate vessel, for example a tissue culture plate. The cells may be seeded at an appropriate density, for example, at a sufficient density to divide and form a confluent monolayer, or an almost confluent monolayer, for example about 80% to about 90% confluence, by about day 6 to about day 10 of differentiation, or by about day 6 or about day 7 of differentiation. For example, the iPSC may be seeded at a density of about 5 000 viable cells/cm$^2$ to about 10 000 viable cells/cm$^2$, or about 7 000 viable cells/cm$^2$ to about 9 000 viable cells/cm$^2$, or about 8 000 viable cells/cm$^2$.

Rho kinase (ROCK) inhibitor (Y-27632, Calbiochem, Merck, Darmstadt, Germany) may be included with iPSC when suspending for seeding. For example, about 1 µM to about 25 µM, about 5 µM to about 15 µM, or about 10 µM ROCK inhibitor may be included with the suspension of iPSC when seeding the iPSC prior to differentiation. ROCK inhibitor may improve survival of the iPSCs when single cell suspensions of pluripotent stem cells are seeded.

In order to induce differentiation, the undifferentiated iPSC is cultured with renal epithelial cell culture medium for differentiation. The renal epithelial cell culture medium may be any growth medium designed to support the growth of renal epithelial cells and that contains nutrients and factors required to maintain attachment, growth and proliferation of renal epithelial cells. The renal epithelial cell culture medium may contain essential factors selected to allow for expansion and survival of a renal cell culture such as PTCs, for example fetal calf serum (FCS), growth factors such as epidermal growth factor (EGF), insulin, hydrocortisone, epinephrine, and triiodothyronine (T3) and transferrin.

Renal epithelial cell culture media are known and may be commercially available, including renal epithelial cell basal medium (REBM) and renal epithelial cell growth medium (REGM BulletKit, available from Lonza Bioscience, Singapore).

For example, Lonza Bioscience REGM™ BulletKit™ (CC-3190) may be used, which includes 500 ml renal epithelial cell basal medium supplemented with 0.5 ml hEGF; 0.5 ml hydrocortisone; 0.5 ml epinephrine; 0.5 ml insulin; 0.5 ml triiodothyronine; 0.5 ml transferrin; 0.5 ml GA-1000; and 2.5 ml FBS.

For example, ATCC renal epithelial cell growth kit (ATCC PCS-400-040) may be used, which includes renal epithelial cell basal medium supplemented with 1.00 µM epinephrine, 10 ng/ml recombinant hEGF, 5 µg/ml recombinant human insulin, 10 nM Triiodothyronine, 100 ng/ml hydrocortisone hemosuccinate, 2.4 mM L-Ala-L-Gln, and 5 µg/ml transferrin.

In addition to the renal epithelial cell culture medium, an extracellular matrix (ECM) molecule is included in the growth conditions in order to induce the undifferentiated iPSC to differentiate into a PTC-like cell.

Thus, the iPSC may be seeded onto a culture surface coated with one or more ECM molecules to mimic the epithelial basement membrane. Each of the one or more ECM molecules may be any ECM molecule that supports the growth and differentiation of iPSCs in renal epithelial cell culture medium. For example, the ECM molecule may be fibronectin, laminin, collagen type IV or MATRIGEL™ (BD Biosciences). MATRIGEL™ Matrix is a solubulized basement membrane preparation extracted from EHS mouse sarcoma and comprises various basement membrane components and bound growth factors that are known to promote the establishment of epithelial tissues, including laminin, collagen IV, heparan sulfate proteoglycans and entactin. In some embodiments, the ECM molecule is MATRIGEL™ Matrix, including growth factor reduced MATRIGEL™ Matrix.

Prior to addition of the one or more ECM molecules to the culture surface, the ECM molecules may be diluted with a renal epithelial cell culture medium, such as REBM. For example, the ECM molecule may be diluted about 10-fold to about 50-fold prior to coating onto the culture surface. The ECM molecule may be diluted using chilled (e.g. ice-cold) renal epithelial cell culture medium.

The seeded iPSC is allowed to attach to the coated culture surface. Subsequent to attachment, the renal epithelial cell culture medium is exchanged for fresh medium, for example about 12 to about 24 hours after seeding, or about 12 to about 16 hours after seeding, or about 16 hours after seeding. Once the cells have attached, the fresh medium may be free from ROCK inhibitor.

In addition, the fresh renal epithelial cell culture medium added after attachment of the iPSC to the ECM molecule-coated culture surface is supplemented with bone morphogenic proteins BMP2 and BMP7. BMP2 and BMP7 may play roles in directing differentiation of the iPSC toward the PTC-like cell type, and thus may increase the number of PTC-like cells obtained during the differentiation method.

For example, from about 1 ng/ml to about 25 ng/ml or from about 2.5 ng/ml to about 15 ng/ml, or about 10 ng/ml BMP2 may be included in the culture medium.

For example, from about 0.25 ng/ml to about 10 ng/ml or from about 1 ng/ml to about 5 ng/ml, or about 2.5 ng/ml BMP7 may be included in the culture medium.

The iPSC is grown in the renal epithelial cell culture medium in the presence of the ECM molecule for a time period of about 8 to about 10 days and at a temperature and under growth conditions sufficient to induce differentiation of at least some of the iPSC present in the culture to a PTC-like cell. For example, for human iPSC, the cell may be differentiated at 37° C., under 5% $CO_2$. During the differentiation period, the cells should attach to the culture surface that has been coated with one or more ECM molecules, and should expand and propagate to eventually form a monolayer, that may be from about 80% to about 100% confluent.

Once seeded for differentiation, the iPSC are cultured without further passaging, in order to obtain the differentiated PTC-like cell. That is, ideally, prior to or by the end of the differentiation period, the culture should be about 80% to about 100% confluent, or about 90% to about 100% confluent. For example, the culture may be about 80% to about 100% confluent by day 6 or day 7 of differentiation. Without being limited to any theory, confluency or near confluency may be involved in promoting differentiation.

Although the culture is not further passaged during the differentiation period, the renal epithelial cell culture medium may be changed for fresh medium throughout the differentiation period. For example, the medium may be changed every day or every other day. The fresh medium may include BMP2 and BMP7, as described above.

It will be appreciated that the precise conditions used for the differentiation period may depend on the organism from which the iPSC was obtained. For human iPSC, for example, during the differentiation period, the cells may be cultured up to 10 days, for example from 8-10 days at 37° C. with 2-10% $CO_2$, or 5% $CO_2$.

The seeding of the initial iPSC is counted as day 0. The addition of medium supplemented with BMP2 and BMP7 is day 1 of differentiation. The end of the differentiation period is about day 8 to about day 10. Confluence or near confluence should be obtained prior to the end of the differentiation period, for example about day 6 to about day 8, or about day 6 to about day 7.

As indicated above, as the iPSC population undergoes differentiation, PTC-specific markers will be expressed by the cells in the culture.

When hiPSC are used, of particular note are the relatively high expression levels of OAT3 observed in the HPTC-like cells obtained from hiPSCs according to the presently described method. This protein is one of the major drug transporters in renal proximal tubular cells and would be important for in vitro nephrotoxicity studies.

OAT3 is expressed in vivo in human PTCs, but is usually expressed at substantially lower levels in HPTCs in vitro, and currently there is no known method to enhance OAT3 expression to levels similar to in vivo expression levels in such primary cells cultured in vitro. OAT3 is also expressed only at very low levels in day 20 hESC-derived HPTC-like cells.

The duration of the differentiation period in the method appears to be important and appears to affect the characteristics of the final differentiated cells obtained. That is, whereas HPTC-like cells derived from hESCs using previously described protocols may be harvested as late as day 20 of differentiation, for human iPSC-derived HPTC-like cells obtained by the currently described methods exhibit an HPTC-like phenotype at about days 8-10 of differentiation. If the differentiation period is too short, the cells will not be differentiated yet and will not be PTC-like. On the other hand, if differentiation of the cells is performed for too long, the cells may start to undergo transdifferentiation, showing decreased expression of PTC markers, including for example OAT3, and increased expression of other, non-PTC markers, for example myofibroblast markers such as alpha-smooth muscle actin (alphaSMA). Typically, the monolayer becomes disrupted, with some cells forming aggregates and even tubule-like structures.

Using human iPSC, it has been observed that after more than about 8-10 days of differentiation, the iPSC-derived culture tends to exhibit a decrease in expression of PTC-specific markers, shows increased expression of mesenchymal markers and the cells start to express the myofibroblast marker alphaSMA at increasing levels. It should be noted that HPTC-like cells as well as HPTC always seem to express alphaSMA and mesenchymal markers to a certain extent under in vitro conditions. An increase in expression of mesenchymal markers and alphaSMA after day 10 is consistent with epithelial to mesenchymal transition and trans-differentiation into myofibroblast-like cells. There are a number of transition stages cells undergo when trans-differentiating to myofibroblast-like cells as compared to PTCs.

Cells with a marked myofibroblast-like phenotype that express only low levels of PTC-specific markers are not useful for applications that require PTC. As well, cells that trans-differentiate to myofibroblast-like cells tend to form aggregates, which then disrupt the monolayer in a process associated with tubule formation (for example at day 14). Such structures would not be compatible with applications such as for example bio-artificial kidneys or high-content screening in drug testing.

That is, after about 8 days, the population may exhibit a large proportion (for example, about 90% or greater) of cells expressing cell markers typical of PTCs. Marker expression is optimal at around days 8-10, and may start to deteriorate rapidly afterward this point. For example, even at day 12-14, the marker expression profile may already begin to noticeably deteriorate, levels of alphaSMA expression rising significantly at these later time points.

Transdifferentiation followed by tubule formation on the substrate surface have been previously described with respect to HPTCs (Zhang et al., Biomaterials 30 (2009) 2899; and Zhang et al., J Cell Mol Med 15 (2011) 1287). In the present methods, it appears that HPTC-like cells derived from hiPSCs also undergo transdifferentiation followed by formation of tubule-like structures on the substrate surface, again underlining similarities between these cells and HPTCs. As indicated above, hESC-derived HPTC-like cells may be harvested even at day 20 of differentiation; in contrast, by day 20, large fractions, of the hiPSC-derived cells are not in an HPTC-like state anymore.

Thus, a differentiation period of about 8 to about 10 days appears to be optimal when using human iPSCs to produce HPTC-like cells, particularly when using a seeding density of about 8 000 cells/cm$^2$ and ROCK inhibitor during seeding. The first day of differentiation (d1) is counted as the first addition of BMP2 and BMP7 to the culture, as described above. It should be noted that the timing of the differentiation period may be influenced by the seeding density of the initial culture. Thus, to obtain HPTC-like cells on day 8 of differentiation, the hiPSCs may be seeded at a density of about 8000 viable cells/cm$^2$ with ROCK inhibitor.

It will be appreciated that when the method is performed on a cell population such as a cell culture, not every cell within the population or culture will necessarily differentiate to a PTC-like cell. Thus, some cells within the population or culture may not differentiate and may retain their iPSC nature while other cells within the same population or culture are induced to differentiate and to become PTC-like.

Thus, the present method may result in differentiation of a population of iPSCs to PTC-like cells, which PTC-like cells may express, for example, KSP-CAD, AQP-1, PEPT1, OAT3 and/or GLUT1.

For example, after the differentiation period, at least 30% of the cells may express PTC-specific markers, or at least 40%, at least 50%, at least 60%, at least 70%, at least 80%, at least 90% of the cells in the population may express PTC-specific markers. For example, from about 30% to about 95%, or from about 50% to about 90% PTC-like cells, or about 80% or greater, about 85% or greater, about 90% or greater, or about 95% or greater, of the cells in the population of PTC-like cells may express PTC-specific markers, including for example OAT3. In one embodiment, about 90% or greater of the cells express PTC-specific markers, including for example OAT3.

The extent of differentiation to PTC-like cells may be readily determined by a skilled person using standard methodology, including as described in the Examples below, such as immunohistochemical techniques, fluorescence activated cell sorting (FACS), Western blot techniques and qPCR techniques to confirm expression of particular marker genes and proteins. Furthermore, similarity between the differentiated cell population produced by the method of the present invention and human primary renal proximal tubule cells may be demonstrated by testing for transporter activity, drug response, enzymatic activities, responsiveness to parathyroid hormone and by other functional assays.

FIG. 1 depicts a flow chart representing an embodiment of the differentiation method, followed by use of the differentiated cell population in an in vitro toxicology method. In the embodiment depicted in FIG. 1, hiPSC are seeded into multi-well plates on day 0; on day 1 the differentiation medium containing BMP2 and BMP7 is added; the cells differentiate during the following week into HPTC-like cells and can be used for drug testing in the evening of day 8; after drug exposure over night the cell lysates are harvested in the morning of day 9 for determining IL6 and IL8 levels by qPCR. In addition to the steps depicted in FIG. 1, the differentiation method may be combined with toxicity screening in other ways. For example, drug exposure could commence on day 8, could be performed for a longer period of time, and/or could be followed by additional assays. In addition, the differentiated cells may be used directly in other assays other than toxicity screening, including for example phosphate reabsorption and drug efficacy.

Thus, in some embodiments, some or all of the following conditions and protocols may be used for differentiation of iPSCs, including human iPSCs.

In comparison to previously reported differentiation protocols, it has been found that the iPSCs, including hiPSCs, may exhibit optimal differentiation (as determined for example by percentage of cells exhibiting renal and PTC-specific markers and by the subset of markers expressed or not expressed) when the following conditions are included in the differentiation protocol. The extracellular matrix component used may be growth factor reduced (GFR) Matrigel, diluted in chilled (e.g. ice-cold) renal epithelial cell basal medium (REBM; available for example from Lonza Bioscience). As indicated above, the propagation of the iPSCs in the undifferentiated state may be performed in mTeSR1 medium. The transfer of iPSCs to the differentiation conditions may be performed by incubation with an enzyme-containing cell-detachment medium such as Accutase, for example, for about 4 minutes. ROCK inhibitor may be included during seeding of the cells and when cells are in suspension. The iPSCs are seeded in differentiation medium at a density of approximately 8000 viable cells/cm$^2$. Cellular factors bone morphogenic proteins BMP2 and BMP7 may be added to the differentiation conditions following cell attachment to the growth surface, approximately 12-16 hours after seeding. The cells are differentiated for a period of about 8 to about 10 days.

In one embodiment of the method, prior to the differentiation protocol, the iPSCs may be propagated in the undifferentiated state with mTeSR1 medium. For differentiation into HPTC-like cells, single cell suspensions of iPSC may be prepared by incubation for 4 minutes at 37° C., for example using an enzyme-containing cell-detachment medium such as StemPro™ Accutase (Life Technologies). The suspension may then be washed with, and resuspended in, Renal Epithelial Cell Growth Medium (REGM). Whenever the cells are in suspension, 10 μM ROCK inhibitor (Y-27632. Calbiochem) may be added. ROCK inhibitor may also be added to the suspension used for cell seeding. Cells may be seeded into 6-well plates at a density of approximately 8 000 viable cells/cm$^2$ on growth factor reduced Matrigel that was diluted 1:50 with ice-cold Renal Epithelial Cell Basal Medium (REBM; Lonza Bioscience) prior to coating. (For coating, 1 ml of diluted GFR Matrigel may be added to each well of a tissue culture plate for 1 hour at 37° C.). After overnight attachment of the cells (about 12-16 hours), the medium may be replaced by REGM supplemented with 10 ng/ml of BMP2 and 2.5 ng/ml of BMP7, marking day 1 of differentiation. The medium may be exchanged for fresh medium every other day. Cells may be harvested on about day 8.

Thus, as indicated above, the method provides a population of cells that contain differentiated PTC-like cells, derived from the iPSCs.

The PTC-like cells in the population express one or more marker expressed by PTC in vivo, including one or more of VIT D3, SLC34A1, NBC1, Na$^+$/K$^+$ ATPase, KSP-CAD, AQP1, GGT, CD13, OAT1, MEG, OAT3, OCT2, OCTN2, PEPT1, GLUT1, GLUT5, SGLT1, SGLT2, URO-10 and ZO-1. In some embodiments, a PTC-like cell in the population expresses OAT3. In some embodiments, a PTC-like cell in the population expresses AQP1, PEPT1, OAT3 and GLUT1. In some embodiments, a PTC-like cell in the population expresses KSP-CAD, AQP1, PEPT1, OAT3 and GLUT1. In some embodiments, a PTC-like cell in the population expresses Na$^+$/K$^+$ ATPase, AQP1, PEPT1, OAT3. SGLT2, URO10, ZO-1 and GLUT1.

The population may contain a majority of cells that have differentiated to become PTC-like cells. For example, the population may contain at least 30% PTC-like cells, at least 40% PTC-like cells, at least 50% PTC-like cells, at least 60% PTC-like cells, at least 70% PTC-like cells, at least 80% PTC-like cells, or at least 90% PTC-like cells. The population may contain from about 30% to about 95%, or from about 50% to about 90% PTC-like cells, or about 80% or greater, about 85% or greater, about 90% or greater, or about 95% or greater PTC-like cells.

The population contains cells that originate from an iPSC. Thus, in addition to the PTC-like cells, the population may also contain non-differentiated iPSCs, partially differentiated iPSCs, as well as some transdifferentiated cells, for example cells that have an increased expression of a myofibroblast marker, such as alphaSMA. Preferably, the population contains very few or no transdifferentiated cells.

The iPSC-derived PTC-like cells, when compared to PTC cultivated in vitro, may exhibit similar characteristics under similar in vitro conditions.

Using human iPSCs, it was found that in the differentiated population, a high degree of cells appear to be hiPSC-derived HPTC-like cells, in some cases with about 90% or greater of cells expressing various renal and HPTC markers by day 8, including AQP-1, as described in the Examples below. Cultures of HPTC are usually more variable; in particular, in vitro HPTC often express OAT3, a major drug transporter, at very low levels. OAT3 tends to be expressed in HPTC-like cells derived by hiPSC by the method disclosed herein, for example as quantified by qPCR and immunostaining results. It should be noted that the levels of various markers expressed may depend on the iPSC line used. For example, OAT3 may be expressed at levels higher than those in HPTC in iPS(Foreskin)-4-derived cells such as those used in Example 2 below. In other HPTC-like cells derived from the different iPSC lines, OAT3 levels may be lower. Similar results may be observed with different PTC-specific markers. As well, GGT expression and activity may be low in hiPSC-derived HPTC-like cells as compared to HPTCs.

In comparison, HPTC-like cell populations derived from differentiation of hESCs are typically in the range of about 30% AQP1 expression (Narayanan et al., 2013). This suggests that HPTC-like populations derived from hESCs contain a more diverse mix of different cell types, which may require further purification.

Thus, the use of iPSCs to yield differentiated PCT-like cell populations provides a good source of cells for various applications, both in vivo and in vitro. These cells are sensitive to nephrotoxicants that are directly toxic for PTC in vivo and can be applied in in vitro models for nephrotoxicology.

The current cell populations may reduce or avoid difficulties sometimes associated with primary cell cultures, such as shortages of human kidney samples, variability between cell populations obtained from different donors, and functional changes that occur in primary cells during passaging. As well, the cell populations differentiated from iPSCs by the methods described herein may reduce or avoid problems associated with populations differentiated from embryonic stem cells. The use of human embryonic stem cells may face ethical and legal considerations. As well, the methods involving embryonic stem cells tend to be more time consuming and may yield a lower percentage of differentiated cells.

Due to the high purity of the iPSC-derived PTC-like cells in the population, the population may be used directly in in vitro assays. For example, tissue culture plates used to differentiate the iPSCs into PTC-like cells may be used for nephrotoxicology studies, without any need for harvesting the cells and replating.

As indicated above, the cells may be used directly in a variety of different in vitro assays without the need for processing, harvesting, purifying or sorting. Beginning at about day 8 to about day 10, the cells can be used in an in vitro assay such as toxicity screening, or other assays such as phosphate reabsorption and drug efficacy, for example. The cells may be used in successive assays, for example, in vitro toxicity screening followed by an additional assay.

Thus, the differentiation method may be designed with a subsequent in vitro assay in mind. If differentiation is performed for 8 days, then the combined time to complete cell differentiation and subsequent overnight drug testing procedures may be as little as 9 days. As depicted in FIG. 1, the cells differentiate into PTC-like cells and can be used for drug testing by the evening of day 8; after drug exposure over night the cell lysates may be harvested in the morning of day 9 for analysis, such as determining IL6 and IL8 levels by qPCR.

As described in the examples below, human iPSCs were used to exemplify the method. Upon differentiation, the differentiated cells expressed markers typical for human kidney cells and human primary renal proximal tubular cells (HPTCs). The hiPSC-derived HPTC-like cells were tested in models for in vitro nephrotoxicology. The data suggested that the predictability of the in vitro models for nephrotoxicology was high when hiPSC-derived HPTC-like cells were applied in these models. The results obtained with hiPSC-derived cells appeared to be at least as good as those obtained with HPTCs and hESC-derived HPTC-like cells. Thus, hiPSC-derived renal cells might be the most suitable cell type to date for applications in in vitro nephrotoxicology, renal tissue engineering and regenerative medicine.

Thus, there is provided a method of screening for nephrotoxicity of a compound. Briefly, the method comprises contacting a test population of PTC-like cells differentiated from iPSCs as described and examining the test population of cells with a test compound that is to be assessed for proximal tubular (PT) toxicity. Subsequent to the contacting, a particular characteristic or phenotype of the cell population is observed and/or measured and compared to the same characteristic or phenotype in a control population of cells that has not been contacted with the test compound.

For example, cells are exposed to a test compound for a given length of time, and then cell viability or cell numbers may be observed following treatment. Other characteristics, phenotypes or endpoints may be assessed, for example, expression of particular genes such as interleukin (IL)-6 and IL-8, as well as changes in cell morphology and cytoskeletal components, and translocation of the nuclear factor (NF) kappaB, ATP depletion and mitochondrial damage, glutathione (GSH) depletion, lactate dehydrogenase (LDH) leakage (membrane damage), generation of reactive oxygen species (ROS) and DNA damage (genotoxicity).

The effect of a test compound may be compared to treatment with a known toxicant that is directly toxic for PTC in vivo, or that is nephrotoxic, but not directly toxic for PTC in vivo, or that is not nephrotoxic.

Conveniently, the test population of cells may be used directly from the differentiation method, without further passaging or harvesting. This approach is convenient, and may also provide good quality of PTC-like cells, with a high proportion of cells that have not yet started to transdifferentiate. It should be noted that harvesting and reseeding may lead to a decline of PTC-specific marker expression.

Or, the cells may be harvested, split and then cultured in any format, including as a confluent monolayer, a subconfluent monolayer, a confluent epithelium, an organoid culture, a confluent 2D culture, an in vitro tubule, a 3D organoid culture, or a 3D culture including a static 3D culture or a 3D culture kept under microfluidic conditions.

In some embodiments, the cells are grown in a monolayer, such as a confluent or subconfluent monolayer. It should be noted that at cell densities of confluent monolayers, good cell differentiation can be achieved.

For example, the differentiated cells may be seeded at high density (e.g. 50 000 cells/cm$^2$) in multi-well plates and then cultivated for 3 days prior to contacting with the compound in order to provide the cells time to form a differentiated epithelium, which would be in the form of a confluent monolayer epithelium (as opposed to sub-confluent or multi-layered that may be used in other embodiments). As noted above, harvesting and reseeding may lead to cells that have reduced PTC-specific marker expression.

In some embodiments, the cells may be directly differentiated or grown in microfluidic bioreactors, including in the form of a confluent monolayer or 2D confluent epithelium. A microfluidic bioreactor may be useful for long-term cultivation and repeated exposure to a test compound, as described herein. This format may be useful for generating compound concentration gradients within the culture.

In the assay method, the in vitro cultured cells are contacted with a compound that is to be tested for potential toxicity to PTC in vivo.

The test compound may be any compound that is to be assessed for PT toxicity. The test compound may be any compound that is expected to come into contact with a subject, including being absorbed or ingested by a subject. For example, the test compound may be a pharmaceutical compound, an organic compound, a pesticide, an environmental toxicant, a heavy metal-containing compound, an organic solvent, a food additive, a cosmetic ingredient or a nanoparticle.

The contacting may be done by adding the compound to the tissue culture medium in which the cells are cultured.

The contacting may be done over a period of time, for example by incubating the compound that is to be tested with the cells in culture. The contacting may be performed for about 8 hours or longer, for about 16 hours or longer, for 24 hours or longer, for 72 hours or longer. Contacting with the test compound may be performed overnight, for example for between about 8 hours and 16 hours, or even longer.

The concentration of the test compound to be used may be varied, and may depend on the compound that is to be tested. Typically, when toxicity is observed in vitro in PTC-like cells at concentrations from about 1 µg/ml to about 1000 such toxicity tends to be predictive of PTC toxicity in vivo at clinically relevant concentrations.

For example, the test compound may be contacted with the test population of cells at a concentration of about 0.001 µg/ml or higher, about 0.01 µg/ml or higher, about 0.1 µg/ml or higher, about 1 µg/ml or higher, about 10 µg/ml or higher, about 100 µg/ml or higher, or about 1000 µg/ml or higher. The test compound may be contacted with the population of cells at a concentration of from about 0.001 µg/ml to about 1000 µg/ml, from about 0.005 µg/ml to about 1000 µg/ml, or from about 0.01 µg/ml to about 500 µg/ml.

As will be appreciated, the control population of differentiated PTC-like cells, although not contacted with the test compound, may be contacted with a negative control solution, for example the solvent or solution used to dissolve the test compound for contacting with the test population (vehicle control).

The contacting may be repeated. For example, the contacting may be performed two or more times, three or more times, four or more times or five or more times over a given period of time.

For example, after the first period of contacting is completed, the tissue culture medium may be replaced with fresh medium that contains the compound. Alternatively, the medium may be replaced with fresh medium that does not contain the test compound, and after a period of time with no contact, the test compound may then again be contacted with the test population of cells.

The contacting thus may be repeated one or more additional times (beyond the first instance of contacting), for example over a period of about 3 to about 28 days. The interval without any contact of test compound (i.e. exposing the cells to fresh medium) may last, for example, for one day to 14 days between the periods of contacting.

The contacting may be repeated shortly before or immediately before the observing and/or measuring.

Various different nephrotoxicology assays are known, and any characteristic, phenotype or endpoint from a nephrotoxicology in vitro assay can be assessed in the assay method. As indicated above, the characteristic or phenotype that is observed and/or measured may be, for example, cell viability, cell number, gene expression levels, including expression of IL-6 and/or IL-8, changes in cell morphology, arrangement of cytoskeletal components, translocation of cellular factors, including translocation of NF-kappaB, ATP depletion, mitochondrial damage, glutathione depletion, membrane damage, including amount of LDH leakage, generation of reactive oxygen species and also DNA damage.

Thus, the cell population may be differentiated from iPSCs and then used to rapidly assess toxicity of test compounds, including potential drug candidates during drug development, in as short a time as 9 days. The sensitivity, specificity and balanced accuracy values for assays performed with hiPSC-derived HPTC-like cells using the methods described herein may be, for example, approximately 85%, 91% and 88%, respectively, as demonstrated in Example 2 below (see Table 4).

For comparison, previous to the current methods, the most rapid alternative protocol for the generation of stein cell derived cells expressing proximal tubular markers covers a period of about 12 days after seeding. That prior protocol involves various steps and a five-fold higher seeding density in comparison to the protocol described here. No results on the purity or quantities of more well-differentiated stem cell-derived cells of the renal lineage generated with alternative protocols have been described and no applications based on such cells have been developed.

The iPSC derived PTC-like cells have a higher degree of purity than hESC-derived cells, which may result in improved overall predictivity using the iPSC derived PTC-like cells. For instance, the balanced accuracy obtained with hESC-derived cells was 0.76, whereas we obtained here a balanced accuracy of 0.88, as set out in Example 2 below.

This improvement in predictivity may be due not only to the quality of the cells, but also due to the combination of the in vitro model with machine learning.

That is, when the in vitro assay method using the PTC-like cells described herein is combined with machine learning techniques, an improved level of predictivity of PTC-toxicity may be achieved.

Machine learning plays an increasingly important role in predicting drug induced toxicity. Support vector machine (SVM) classifier methods and learning algorithms that involve pattern recognition, classification and regression analysis are known, and the SVM classifier has been identified as a valuable tool. Using this classifier, large data sets can be efficiently analysed without manual intervention, and this method is preferable compared to other methods that are more prone to biases. In agreement with other findings, when used in the present assay methods, SVM-based classification was shown to result in high accuracy, as described in Example 2 below.

In addition to the described in vitro assay methods, PTC-like cells may be applied in bioartificial kidneys to replace PT functions, and for production of renal tubules, including human renal tubules generated in vitro in gels or on two-dimensional (2D) surfaces.

The present invention provides a bioartificial kidney containing PTC-like cells differentiated from iPSCs, which device may be used for the treatment of lost kidney function.

Generally, bioartificial kidneys contain two hollow fibre cartridges. One is used for hemofiltration, whereas the second one is a bioreactor containing renal cells. Such devices are known in the art and may be connected to a patient as in the manner of a hemodialysis or hemofiltration device.

For example, in such a device a hollow-fiber hemofiltration cartridge with a membrane surface may be used as a scaffold for cell growth. iPSCs can be seeded onto the inner or outer surface and differentiated as described above. Alternatively, differentiated iPSC-derived cells can be seeded on the surface.

Thus, there is provided a method of preparing a device, the method comprising differentiating iPSCs into PTC-like cells as described above, either before or after seeding the cells in a hollow fibre device.

By placing the presently described cells within such a device, the cells may be used in clinical applications while being separated by blood circulation via semi-permeable membranes as artificial immunological barriers, reducing risk of immune rejection or other immune complications and risk of possible tumorigenesis which may occur when undifferentiated stem cells enter the bloodstream.

The above described bioartificial kidney may be used to treat a subject having a renal related disorder. The cells within the bioartificial kidney may perform PTC functions, thus replacing or supplementing PTC functions that are compromised or absent in diseased kidneys.

Thus, there is also presently provided a method of treating a renal related disorder in a subject. The method comprises connecting a bioartificial kidney of the present invention to a subject in need thereof.

Treating a renal related disorder refers to an approach for obtaining beneficial or desired results, including clinical results. Beneficial or desired clinical results can include, but are not limited to, alleviation or amelioration of one or more symptoms or conditions, diminishment of extent of disorder or disease, stabilization of the state of disease; prevention of development of disorder or disease, prevention of spread of disorder or disease, delay or slowing of disorder or disease progression, delay or slowing of disorder or disease onset, amelioration or palliation of the disorder or disease state, and remission (whether partial or total). "Treating" can also mean prolonging survival of a subject beyond that expected in the absence of treatment. "Treating" can also mean inhibiting the progression of disorder or disease, slowing the progression of disorder or disease temporarily, although more preferably, it involves halting the progression of the disorder or disease permanently.

The subject may be any subject having a renal related disorder or requiring treatment for a renal related disorder. A renal related disorder refers to any disease, disorder or condition which may cause, result in, or is associated with a permanent or transient decline in renal functions, renal degeneration or renal failure, including acute kidney injury, chronic kidney disease, end stage renal disease, nephropathy, diabetic nephropathy, nephrosis, Bright's disease, renal insufficiency, glomerulitis, glomerulosclerosis, or nephritis.

As stated above, such devices and uses of such devices are known in the art. Generally, the device is used in a manner similar to a conventional hemodialysis device or hemofiltration device. The device is connected externally to a subject and the subject's blood and hemofiltrate (produced in the first hollow fiber cartridge) is pumped through the device, past the membrane with the cells seeded on the opposite side of the membrane and then eventually back into the subject. The cells perform proximal tubular functions (see above) as the blood and hemofiltrate from the subject is passed through the device.

There is also presently provided a method of treating a renal related disorder in a subject comprising implanting a cell of the present invention in a subject in need thereof.

The cell may be implanted using standard surgical or injection methods. The cell may be implanted at a suitable site in the subject to provide therapeutic-treatment of the renal related disorder, for example a site where renal epithelial cells are required; including in the renal cortex or proximal tubuli. The cell may be implanted into the cortex of a diseased kidney.

In one embodiment, cells may be implanted in a delivery vehicle, for example a supporting hydrogel. Delivery vehicles for implanting live cells are known, including for example hydrogels, 3D renal matrices, or cell scaffolding such as, for example, polymeric cell supports. Such delivery vehicles may be biocompatible and biodegradable, and may comprise synthetic materials, biomaterials, or a combination thereof.

The cells may be also suitable for bioengineered grafts produced by seeding the cells into a 3D renal matrix. For example, the 3D renal matrix may be designed to mimic the matrix of a human kidney, consisting of one or more synthetic or natural compounds. Techniques such as 3D printing can be used to produce matrices that reflect shape, size and architecture of a human kidney. Undifferentiated iPS may be seeded into the matrix and be differentiated in the matrix according to the methods described herein. Alternatively, differentiated iPS-derived PTC-like cells may be seeded into the matrix. iPS or PTC-like cells may be seeded alone, or together with other cell types, such as other kidney-specific and vascular cell types.

Decellularized matrices may be used, such as decellularized kidneys (Song et al., Nature Medicine, 2013, 19(5), 646-51). Matrices derived from porcine kidneys have a suitable size for transplantation into a human. For example, undifferentiated iPSC may be seeded into the decellularized matrix and be differentiated within the matrix according to the procedures described herein. Alternatively, differentiated iPS-derived PTC-like cells can be seeded into the decellularized matrix. iPS or PTC-like cells can be seeded alone, or together with other cell types, such as other kidney-specific and vascular cell types.

Bioengineered grafts may be used in organ cultures for various applications, including compound efficacy testing and safety screening. Grafts having a small size may be preferred for such applications. For example, grafts that represent only part of the kidney, such as the cortex or proximal tubules, may be used as renal disease models.

As well, bioengineered grafts may be used for transplantation into a human or animal with end stage renal disease.

An effective amount of PTC-like cells, including cells within a bioreactor or bioengineered graft, is administered to the subject. The term "effective amount" as used herein means an amount effective, at dosages and for periods of time necessary to achieve the desired result, for example, to treat the renal related disorder.

The number of total number cells to be administered will vary, depending on several factors, including the severity and type of the renal related disorder, the mode of administration, and the age and health of the subject.

In addition, the PTC-like cells obtained as described herein may be used in other in vitro applications, including for example, producing in vitro tubules or tubule-like structures. For example, methods have been previously described in PCT published application WO 2010/064995.

The methods, cell populations, devices and uses as described herein are further exemplified by way of the following non-limiting examples.

EXAMPLES

Example 1

Treatment of hiPSC-derived HTPC-like cells with 2 test drugs (rifampicin and paraquat, both are nephrotoxicants that are directly toxic for PTC) started on Nov. 5, 2012. The drug response was tested with the nephrotoxicology in vitro model based on interleukin-6/interleukin-8 expression (Li et al., Toxicol. Res. 2 (2013), 352-362). The data revealed an increase in IL-6 (and IL-8 in the case of rifampicin) expression after treatment with the FTC-specific nephrotoxicants. This indicated that treatment with PTC-specific nephrotoxicants resulted in a positive response.

Materials and Methods

All procedures were conducted using aseptic techniques.

Reagents:

mTeSR1 medium kit: STEM CELL Technologies, cat, no. 05850; BD Matrigel™ Basement Membrane Matrix, Growth Factor Reduced (GFR), BD Biosciences, cat no. 356230; Rock-Inhibitor (Y-27632) Calbiochem, cat no. 688000; Renal Epithelial Cell Basal Medium (REBM), Lonza Bioscience, cat.-no. CC-3191; StemPro® Accutase® Cell Dissociation Reagent, 100 ml, Lifetech, cat. no. A11105-01; Renal Epithelial Cell Growth Medium (REGM), Bulletkit, Lonza Bioscience, cat. no. CC-3190; BMP2, R&D systems, cat. no. 355-BM-010; BMP7 R&D systems, cat. no. 354-BP-010; Defined Foetal Bovine Serum (FBS), Thermo. Scientific Hyclone, cat. no. SH30070.03; Dimethyl sulfoxide (DMSO) Sigma, cat. no. D2650.

Propagation of Undifferentiated iPSCs:

Human induced pluripotent stem cell (hiPSC) cultures were grown on 6-well GFR matrigel-coated plates in mTeSR1 medium. (following the manufacturer's instructions) with medium change every day. mTeSR1 medium kit: STEM CELL Technologies, cat no. 05850; BD Matrigel™ Basement Membrane Matrix, Growth Factor Reduced (GFR), BD Biosciences, cat no. 356230.

Differentiation of iPSCs:

By 5-6 days when undifferentiated hiPSC cultures were ~80% confluent, renal differentiation conditions were applied.

Preparation of the Growth Factor Reduced (GFR)-Matrigel-Coated Plates.

GFR-matrigel was diluted 50× in ice-cold REBM (Renal Epithelial cell Basal Medium, Lonza) to the working solution for coating (1 ml of GFR-matrigel working solution in each well of a 6-well plate). The diluted Matrigel was cold (below 10° C.) when coating the plates. The coating was performed by incubating the plate at 37° C. for 1 hour.

After the Matrigel coating time, the hiPSC culture was passaged. Old mTeSR1 medium was removed from hiPSC culture dishes, rinsed two times with sterile 1×PBS and incubated with pre-warmed accutase (1 ml per well of 6-well plate) for 4 minutes at 37° C. By means of 1 ml micropipette, colonies were dissociated into single cells by pipetting up and down a number of times, while avoiding introducing bubbles during the process.

The cell suspension was transferred into a 50 ml falcon tube containing REGM 5× the volume (i.e. 1 ml cell suspension added with 4 ml of REGM) containing 10 µM of Rock-inhibitor. An aliquot of the cell suspension was taken to determine the total cell numbers. Rock inhibitor was present in the solution whenever the cells were in suspension and only during the first 12-16 hours of seeding the cells for attachment.

The cell suspension was centrifuged at 300 g for 5 min to pellet the cells (using a swing bucket centrifuge). During centrifuge the total cell numbers in the total resuspended volume were calculated. The REGM required to resuspend the cells to a concentration of about 8000 cells/cm$^2$ was prepared, containing 10 µM of Rock inhibitor.

After centrifugation, the supernatant medium was removed from the tube and the prepared REGM was added for re-suspending the cells. For 6 well plate, the volume of REGM required was 2 ml per well. The cells were seeded to the plates at the required density and volume, and were then moved as quickly as possible to 37° C., $CO_2$ incubator. Disturbance of the incubator was avoided, as agitation prevents the attachment of required cell density for differentiation. Cell seeding density was strictly maintained and the plates were placed in the incubator after seeding the cells as quickly as possible to avoid any loss of cell viability.

The cells were allowed to attach overnight, before changing the medium to REGM supplemented with 10 ng/ml of BMP2 and 2.5 ng/ml of BMP7.

The differentiation was conducted in REGM with 10 ng/ml of BMP2 and 2.5 ng/ml of BMP7 with medium change every other day. BMP2 and BMP7 were freshly supplemented to the medium prior to addition to the cells.

The first day of differentiation was calculated on the first addition of BMP2 and BMP7 to the cell culture. Differentiation conditions were applied up to Day 8-10. By the end of Day 3, the cell density increased and by the end of Day 6, the cell had formed a monolayer. Cells may differentiate to fibroblast-like cells if no monolayer is formed at this stage. By day 7 to day 8, the cells should form a confluent monolayer with epithelial morphology.

Cryopreservation:

Differentiated cells were cryopreserved following the standard procedure. The cryopreservation medium was prepared as follows: 40% high-grade defined FBS; 50% REGM; 10% DMSO. Cells were cryopreserved at $2 \times 10^6$ cells/ml/cryovial. A standard cryopreservation container was used for optimum freezing condition. Cells were initially kept in −80° C. and the next day the cells were moved to vapor phase of liquid nitrogen storage.

Drug Treatment:

The cryovial was quickly thawed and added to REGM containing 10 µM of Rock-inhibitor. Cells were pelleted and resuspend in fresh REGM containing BMP2 and BMP7 supplements and Rock inhibitor. Cells were seeded at $1 \times 10^5$ cells per cm$^2$ of 24-well plate in REGM supplemented with 10 ng/ml of BMP2 and 2.5 ng/ml of BMP7, and cultured for 3 days, prior to the commencement of drug treatment (following the similar protocol as for primary HPTCs; Li et al., Toxicol. Res. 2 (2013), 352-362). Drugs were dissolved in their respective solvents and added to the REGM at, for example, 1, 10, 100 and 1000 µg/ml.

Instead of using cryopreserved cells, iPSCs can be seeded into the multi-well plate used for drug treatment, and differentiated in this plate into HPTC-like cells using the protocol outlined above. The cells are ready for drug treatment at day 8-10.

Figure 2:
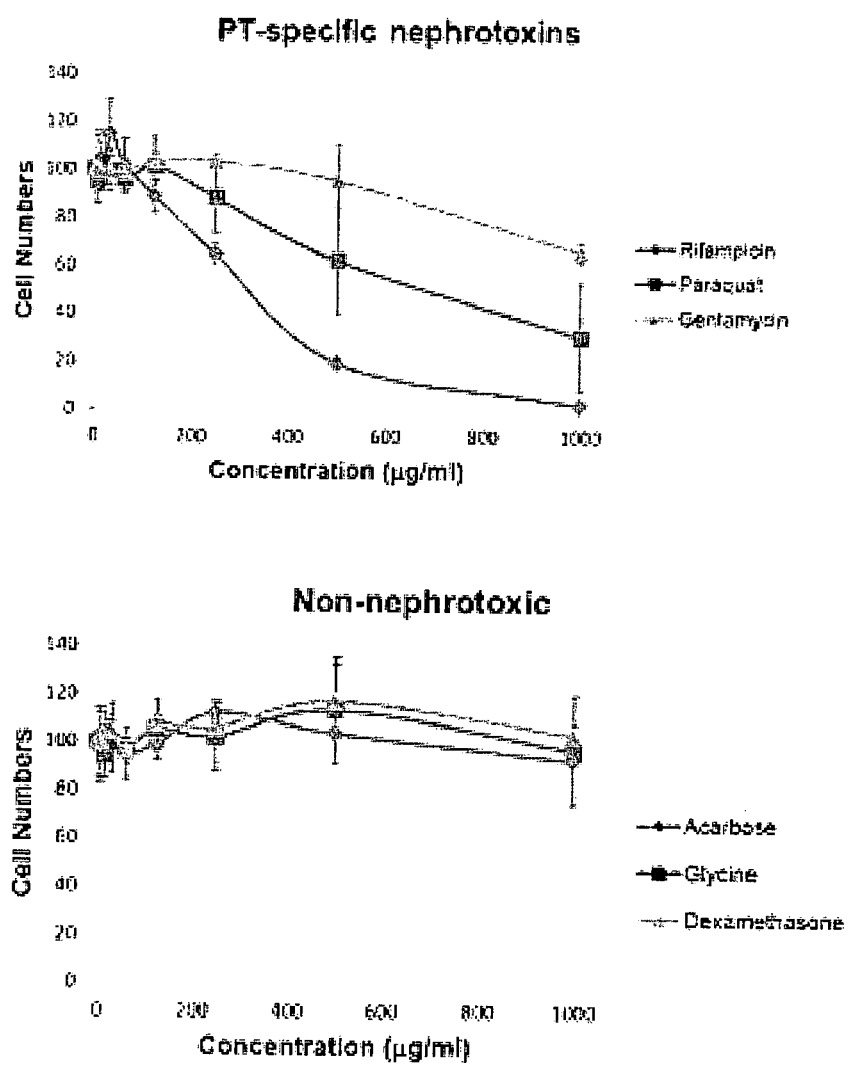
FIG. 2. Impact of drug treatment on the numbers of hiPSC-derived HPTC-like cells.

FIG. 2. Impact of Drug Treatment on the Numbers of hiPSC-Derived HPTC-Like Cells.

HPTC-like cells were obtained from iPS(Foreskin)-4 cells. HPTC-like cells were seeded into multi-well plates and treated with various drug concentrations (x-axis) 3 days after seeding. Cells were treated overnight with PTC-specific nephrotoxins (upper panel) or non-nephrotoxic drugs (lower panel). After drug exposure, cell numbers were determined by high content screening (HCS). All data were normalized to the vehicle controls (100%). Cell numbers did not decrease when HPTC-like cells were treated with non-nephrotoxic drugs. In contrast, cell numbers decreased when the HPTC-like cells were treated with FTC-specific nephrotoxins. In similar experiments performed with HPTCs, a decrease in cell numbers was not observed after treatment with gentamicin and paraquat (Li et al., Toxicol. Res. 2 (2013) 352-362). This might indicate that hiPSC-derived HPTC-like cells are more sensitive than HPTCs.

Results

When the differentiation protocol outlined above was applied, after about 8 days, the population demonstrated a large proportion (e.g. about 90% or greater) of cells expressing cell markers typical of PTCs. In order to determine the optimum range of differentiation culture period, a time course with immunostaining data was performed. All of the markers tested were characteristic for renal proximal tubular cells, except alpha smooth muscle actin (SMA). SMA becomes expressed when renal proximal tubular cells transdifferentiate into myofibroblast-like cells, and such myofibroblast-like cells are not desirable in a PTC-like cell culture. The results showed that marker expression is optimal at around days 8-10, and deteriorates rapidly afterwards. Even at day 12-14, the marker expression profile is already noticeably detoriated. It was observed that SMA expression rises significantly at these later time points.

Whereas HPTC-like cells derived from hESCs using previously described protocols may be harvested as late as day 20 of differentiation, the hiPSC-derived HPTC-like cells obtained by the currently described methods exhibit optimal characteristics at days 8-10 of differentiation.

After 8-10 days differentiation, the iPSC-derived culture exhibited a decrease in expression of PTC-specific markers, and the cells started to transdifferentiate into myfibroblast-like cells.

One of the markers was kidney-specific cadherin (KSP-CAD), which is exclusively transcribed in the kidney. In addition, the following proximal tubular (PT)-specific markers were tested: aquaporin 1 (AQP1), γ-glutamyl transferase (GGT) and organic anion transporter 3 (OAT3). The myofibroblast marker α-SMA was also included.

Expression of KSP-CAD confirmed renal differentiation of the hiPSC-derived cells. The qPCR results were in accordance with the immunostaining data on PTC-specific marker expression and the relatively low levels of GGT activity observed in functional assays. HPTC-like cells derived from both hiPSC lines showed similar patterns of up- or down-regulation of marker genes. In both cases these patterns were different from the patterns obtained with hESC-derived cells.

Alpha-smooth muscle actin (alphaSMA) is a myofibroblast marker that appears to become up-regulated after about day 10: There are a number of transition stages cells undergo when trans-differentiating to myofibroblast-like cells as compared to PTCs. Cells that have entered a myofibroblast-like stage cannot be used for applications that require PTC. As well, cells that trans-differentiate to myofibroblast-like cells tend to form aggregates, which then disrupt the monolayer in a process associated with tubule formation (day 14). Such structures would not be compatible with applications in bio-artificial kidneys or high-content screening in drug testing.

Of particular note is the expression of OAT3 observed at days 8-10 in the HPTC-like cells obtained from iPSCs. OAT3 is expressed in vivo in human PTCs, but is usually expressed at substantially lower levels in HPTCs in vitro, and currently there is no known method to enhance OAT3 expression to levels similar to in vivo expression levels in such primary cells cultured in vitro. OAT3 is also expressed only at very low levels in day 20 hESC-derived HPTC-like cells (see for example Narayanan et al., 2013, FIG. 3).

High proportions of the HPTC-like cell populations obtained by the described methods tend to be differentiated. In some experiments, it has been confirmed by FACS that about 93% of iPSC-derived HPTC express OAT3 at day 8 (AQP1 98%), and also other HPTC-specific markers are >90%. This is in comparison with HPTC-like cell populations derived from differentiation of hESCs, which are typically in the range of about 30% AQP1 expression (Narayanan et al., 2013). This suggests that HPTC-like populations derived from hESCs contain a more diverse mix of different cell types, which may require further purification.

It has been confirmed by FACS that 93% of hiPSC-derived HPTC-like cells express OAT3 at day 8 (AQP1 98%), and also other HPTC-specific markers are >90%. Note that the optimal results with d20 hESC-derived cells are in the range of about 30% AQP1 expression (Narayanan et al., 2013; other markers were not checked by FACS in this publication, but also the immunostaining data for other markers were not as consistent as those obtained with iPSC-derived cells). Thus, the results here show that there are major quantitative and qualitative differences between HPTC-like populations derived from hESCs (as described in Narayanan et al.) and those derived from hiPSCs as described here.

Example 2

A one-step protocol for the differentiation of hiPSC into HPTC-like cells was used for drug testing immediately without prior cell harvesting. Predictive performance of hiPSC-derived cells was determined by evaluating the response to 30 compounds. The results were automatically classified by the support vector machine algorithm. In this way, PTC-toxicity in humans may be predicted with high accuracy. Thus, the combination of the one-step differentiation protocol with machine learning may provide an efficient method for accurate prediction of PTC-toxicity in humans.

Materials and Methods

Expansion and Differentiation of hiPSC:

iPS(Foreskin)-4, iPS IMR90-4 and iPS DF19-9-11T.H cells were obtained from the WiCell Research Institute (Madison, Wis., USA). The work with these hiPSC lines was approved by the Institutional Review Board of the National University of Singapore (NUS-IRB reference code: 13-437). Undifferentiated cells were expanded with mTeSR1 medium (Stemcell Technologies, Singapore) in multi-well plates coated with growth factor-reduced Matrigel (BD, Franklin Lakes, N.J., USA). For differentiation, hiPSC were seeded (day 0) at a density of 8000 cells/cm$^2$ into 24-well plates coated with growth factor-reduced Matrigel. Single cell suspensions were prepared with StemPro Accutase (Life Technologies, Carlsbad, Calif., USA).

Cells were resuspended and seeded with commercial renal epithelial growth medium (REGM BulletKit; Lonza Bioscience, Singapore) supplemented with 10 µm Rho kinase (ROCK) inhibitor (Y-27632, Calbiochem, Merck, Darmstadt, Germany). The medium was exchanged on day 1 against REGM supplemented with 10 ng/ml of BMP2 and 2.5 ng/ml of BMP7 (R&D Systems, Minneapolis, Minn., USA). The BMP-supplemented medium did not contain ROCK inhibitor. The medium was exchanged every other day.

Compound treatment was performed on day 8 and the same plates in which the cells had been differentiated were continued to be used for compound testing. A flow chart of the differentiation procedure with subsequent drug testing is provided in FIG. 1.

Fluorescence-Activated Cell Sorting (FACS) and Immunofluorescence:

FACS and immunofluorescence were performed as outlined previously (Li et al., Toxicol. Res. 2 (2013), 352-362; Narayanan et al., Kidney Int. 83 (2013), 593-603).

Scanning Electron Microscopy (SEM) and Determination of g-Glutamyltransferase 1 (GGT) and Drug Transporter Activity:

These procedures were performed as outlined previously (Tiong et al. Mol. Pharm. 11 (2014), 1933-1948; Narayanan et al., Kidney Int. 83 (2013), 593-603).

Compound Treatment and Determination of IL6 and IL8 Expression levels:

Compound treatment was performed for 16 hours. All compounds, except aristolochic acid, have been used in previous studies and detailed information on nephrotoxicity in humans has been provided (Li et al., Toxicol. Res. 2 (2013), 352-362; Li et al. Mol. Pharm. 11 (2014), 1982-1990). Aristolochic acid (a 1:1 mixture of aristolochic acids I and II) was purchased from EMD Millipore. (Billerica, Mass., USA). Aristolochic acid is a well characterized nephrotoxin that can lead in humans to acute kidney injury associated with direct toxicity to the renal proximal tubules or chronic kidney disease and urothelial cancer (Yang et al., Nephrol. Dial. Transplant. 27 (2012), 292-298).

All compounds were tested at concentrations of 1, 10, 100 and 1000 μg/ml (three replicates each) and all results were normalized to vehicle controls as in previous studies. All plates contained as controls (three replicates each) 100 μg/ml dexamethasone (negative) and 100 μg/ml puromycin (positive). Z' values were calculated as described (Zhang et al. J. Biomol. Screen 4 (1999), 67-73) and plates with Z' values >0.5 were included. IL6 and IL8 mRNA levels were determined by quantitative realtime reverse transcription polymerase chain reaction (qPCR) as before by using the same primers (Table 1). All data were normalized to two reference genes (GAPDH and PPIA).

Table 1 below provides details of the markers used for qPCR. The table lists all markers used for qPCR. The acronyms used are alphabetically listed. Gene IDs and descriptions follow the nomenclature of the HUGO Gene Nomenclature Committee (HGNC). The primer pairs used for qPCR (F: forward, R: reverse) and amplicon sizes in base pairs (bp) are provided.

TABLE 1 qPCR Primers

| Acronym/Gene ID Description | Primer Pairs | SEQ ID NO: | Amplicon (bp) |
|---|---|---|---|
| AQPI/AQP1 Aquaporin 1 | F 5'-AAGCTCTTCTGGAGGGCAGT-3' R 5'-CACCTTCACGTTGTCCTGGACCG-3' | 1 2 | 137 |
| AQP3/AQP3 Aquaporin 3 | F 5'-GACGCTGGGAGCCTTCTTG-3' R 5'-GCTGGTTGTCGGCGAAGT-3' | 3 4 | 80 |
| ATPase/ATP1B1 ATPase, Na+/K+ transporting, beta 1 polypeptide | F 5'-GCTGACCCGCCATCGCCAT-3' R 5'-ACCAACTGCCACCGGTCCTG-3' | 5 6 | 114 |
| CD13/ANPEP Alanyl (membrane) aminopeptidase | F 5'-CACACACCGTTCCTGGATCTCCTCT-3' R 5'-GCTCCAACAGGCGAAGGTCACT-3' | 7 8 | 76 |
| DNMT3B/DNMT3B DNA(cytosine-5-)-methyltransferase 3 beta | F 5'-AGTCCTCAAAGAGTTGGGCATAAA-3' R 5'-ACGGTTCCAACAGCAATGG-3 | 9 10 | 80 |
| E-CAD/CDH1 E-cadherin | F 5'-GAGGACCAGGACTTTGACTT-3' R 5'-AGATACCGGGGGACACTCAT-3' | 11 12 | 107 |
| GAPDH/GAPDH Glyceraldehyde-3-phosphate dehydrogenase | F 5'-ACCCCTTCATTGACCTCAACTACA-3' R 5'-CTTGACGGTGCCATGGAATT-3' | 13 14 | 80 |
| GDNF/GDNF Glial cell derived neurotrophic factor | F 5'-ACTTGGGTCTGGGCTATGAAAC-3' R 5'-TCGTACGTTGTCTCAGCTGCAT-3' | 15 16 | 85 |
| GGT/GGT1 Gamma-glutamyltransferase 1 | F 5'-TGAGCCCAGAAGTGAGAGCAGTTG-3' R 5'-ATGTCCACCAGCTCAGAGAGGGT-3' | 17 18 | 85 |
| GLUT5/SLC2A5 Solute carrier family 2 (facilitated glucose /fructose transporter), member 5 | F 5'-CCCCAGCTCTTCATCACTGTTGGC-3' R 5'-TTTGGAACACAAGGAGGGGCC-3' | 19 20 | 148 |
| HOXD11/HOXD11 Homeobox D11 | F 5'-AAAAAGCGCTGTCCCTATACCA-3' R 5'-TGAGGTTGAGCATCCGAGAGA-3' | 21 22 | 115 |
| IL6/IL6 Interleukin 6 | F 5'-TGGCTGCAGGACATGACAAC-3' R 5'-TGAGGTGCCCATGCTACATTT-3' | 23 24 | 100 |
| IL8/IL8 Interleukin 8 | F 5'-TTGGCAGCCTTCCTGATTTCT-3' R 5'-GGGTGGAAAGGTTTGGAGTATG-3' | 25 26 | 110 |

TABLE 1-continued qPCR Primers

| Acronym/Gene ID Description | Primer Pairs | SEQ ID NO: | Amplicon (bp) |
|---|---|---|---|
| KIM1/HAVCR1 Hepatitis A virus cellular receptor 1 | F 5'-CAGGCTGATCCCATAATGCA-3' R 5'-CTGCCTCTCCACCAACCTTTAC-3' | 27 28 | 100 |
| KSP-CAD/CDH16 KSP-cadherin | F 5'-TCCCATGCCTACCTCACCTT-3' R 5'-TTGCAGCGACACACGATCA-3' | 29 30 | 125 |
| MDR1/ABCB1 ATP binding cassette, subfamily B (MDR/TAP), member 1 | F 5'-GCCCTTGTTAGACAGCCTCATATTT-3' R 5'-GGACAGGCGGTGAGCAAT-3' | 31 32 | 141 |
| MEG/LRP2 Low density lipoprotein receptor-related protein 2 (Megalin) | F 5'-AGACTGGTTCTAACGCCTGTAATC-3' R 5'-GCTCTGTGGGTGGTTCATTGG-3' | 33 34 | 171 |
| NANOG /NANOG Nanog homeobox | F 5'-TCGCAAAAAAGGAAGACAAGGT-3' R 5'-GAGTACACACAGCTGGGTGGAA-3' | 35 36 | 80 |
| NBC1/SLC4A4 Solute carrier family 4 (sodium bicarbonate cotransporter), member 4 | F 5'-CCAAACTGGAGGAGCGACGGAAG-3' R 5'-CACACACATGCTTGAGGAAGGA-3' | 37 38 | 90 |
| N-CAD/CDH2 N-cadherin | F 5'-CCCATACACCAGCCTGGAACGC-3' R 5'-TGGGTCGGTCTGGATGGCGA-3' | 39 40 | 80 |
| NCCT/SLC12A3 Thiazide-sensitive sodium chloride cotransporter | F 5'-CACCAAGAGGTTTGAGGACATG-3' R 5'-GACAGTGGCCTCATCCTTGAA-3' | 41 42 | 70 |
| NGAL/LCN2 Lipocalin 2 | F 5'-CAAGGAGCTGACTTCGGAACTAA-3' R 5'-TGCACTCAGCCGTCGATACA-3' | 43 44 | 120 |
| NKCC2/SLC12A1 Solute carrier family 12 (sodium/potassium/chloride transporter), member I | F 5'-TGGGGAGTCATGCTCTTCATTCGC-3' R 5'-CCACGAACAAACCCGTTAGTTGC-3' | 45 46 | 149 |
| OAT1/SLC22A6 Solute carrier family 22 (organic anion transporter), member 6 | F 5'-TCTACTCCTGGTTCTTCATTG-3' R 5'-CGGAGTACCTCCATACTCAAT-3' | 47 48 | 142 |
| OATS/SLC22A8 Solute carrier family 22 (organic anion transporter), member 8 | F 5'-GCCCTTGGACTTGCAGACCG-3' R 5'-ACCTGTTTGCCTGATGACTG-3' | 49 50 | 127 |
| OCT2/SLC22A2 Solute carrier family 22 (organic cation transporter), member 2 | F 5'-GCTGTACCCCACATTCATTAGGA-3' R 5'-GGGAGCTCAAGCCAGATGTTA-3' | 51 52 | 120 |
| OCT3/4/POU5F1 POU class 5 homeobox 1 | F 5'-GGAGGAAGCTGACAACAATGAAA-3' R 5'-GGTTGCCTCTCACTCGGTTCT-3' | 53 54 | 110 |
| OCTN2/SLC22A5 Solute carrier family 22 (organic cation/carnitine transporter), member 5 | F 5'-GGTTTGGCCGGAAGAATGT-3' R 5'-CCATGCCTACAAGGACAAACAG-3' | 55 56 | 120 |
| OSR1/OSR1 Odd-skipped related transcription factor 1 | F 5'-CCCTGCAGCTCACCAACTACT-3' R 5'-AGATGGTCCGAAGGCACTGT-3' | 57 58 | 70 |
| PAX2/PAX2 Paired box 2 | F 5'-CTTCCAGGCATCAGAGCACAT-3' R 5'-GTGGATGCAGATAGACTCGACTTG-3' | 59 60 | 105 |
| PEPT1/SLC15A1 Solute carrier family 15 (oligopeptide transporter), member 1 | F 5'-CAGTGGGCCGAGTACATTCTATT-3' R 5'-TCTCCGCTGGGTTGATGTAAG-3' | 61 62 | 100 |

TABLE 1-continued qPCR Primers

| Acronym/Gene ID Description | Primer Pairs | SEQ ID NO: | Amplicon (bp) |
|---|---|---|---|
| PODXL/PODXL Podocalyxin-like | F 5'-ACCTACCCTGCCAGAGACCAT-3'<br>R 5'-AGATCCTCACACTTTGCCCAGTT-3' | 63<br>64 | 120 |
| PPIA/PPIA Peptidylprolyl isomerase A (cyclophilin A) | F 5'-GTGCATGCCTAGTCCTAGCTGAT-3'<br>R 5'-CTCACTCTAGGCTCAAGCAATCC-3' | 65<br>66 | 64 |
| SGLT2/SLC5A2 Solute carrier family 5 (sodium/glucose cotransporter), member 2 | F 5'-ACGCCTGATTCCCGAGTTCT-3'<br>R 5'-AGAACAGCACAATGGCGAAGT-3' | 67<br>68 | 110 |
| SIX2/SIX2 SIX homeobox 2 | F 5'-AGGAAAGGGAGAACAACGAGAA-3'<br>R 5'-GAGCTGCCTAACACCGACTTG-3' | 69<br>70 | 82 |
| SLC34A1/SLC34A1 Solute Carrier Family 34 (Type II Sodium/Phosphate Contransporter), Member 1 | F 5'-CTGGGTCACAGGCTACTTTGC-3'<br>R 5'-GCCCTCTCAATGCTGATCACA-3' | 71<br>72 | 126 |
| SMA/ACTA2 Actin, alpha 2. smooth muscle, aorta | F 5'-TCATCACCAACTGGGACGAC-3'<br>R 5'-ATGCTCTTCAGGGGCAACAC-3' | 73<br>74 | 80 |
| SOX2/SOX2 SRY (sex determining region Y)-box 2 | F 5'-ATCCCATCACCCACAGCAA-3'<br>R 5'-GTCGGCATCGCGGTTTT-3' | 75<br>76 | 81 |
| T/T Brachyury | F 5'-GGGTCCACAGCGCATGAT-3'<br>R 5'-TTTAAGAGCTGTGATCTCCTCGTT-3' | 77<br>78 | 95 |
| UMOD/UMOD Uromodulin | F 5'-TGGCTTCAGGACACCAGACATCAG-3'<br>R 5'-AGCACCTGCCCAAAGGAAAGACG-3' | 79<br>80 | 77 |
| VIM/VIM Vimentin | F 5'-ACCTGAGGGAAACTAATCTG-3'<br>R 5'-CGTTGATAACCTGTCCATCT-3' | 81<br>82 | 105 |
| VIT D3/CYP27B1 Cytochrome P450, family 27, subfamily B, polypeptide 1 (synthesizes 1alpha,25-dihydroxyvitamin D3) | F 5'-GGAAATTCTCGTGTCCCAGA-3'<br>R 5'-TGACACAGAGTGACCAGCGTA-3' | 83<br>84 | 80 |
| WT1/WT1 Wilms tumor 1 | F 5'-AACAGCAACAGCAAGAAATAAATCA-<br>R 5'-GACCTCGGGAATGTTAGACAAGAT-3' | 85<br>86 | 71 |
| ZO-1/TJP1 Tight junction protein 1 | F 5'-GAGAGGATTTGTCCGCTCAG-3'<br>R 5'-AGGCCTCAGAAATCCAGCTT-3' | 87<br>88 | 86 |

Determination of Marker Expression Levels:

Marker expression levels were determined by qPCR as described (Li et al., Toxicol. Res. 2 (2013), 352-362). Details of primers and amplicons are provided in the Table 1 above.

Calculations and Statistics:

All calculations and statistics that were not part of the computational analysis described herein were performed with Microsoft Office Excel 2010. The unpaired t-test (Microsoft Office Excel 2010) was used for statistics. The normal distribution of the data was confirmed using SigmaStat (3.5) (Systat Software Inc., Chicago, Ill., USA).

Computational Analysis:

For each drug, the IL6 or IL8 expression values measured at all doses were normalized to the respective vehicle controls. Then, log 2 transformation was applied to the resulting ratios, a three-parameter log-logistic model with lower limit=0 was used to obtain a sigmoidal dose response curve (Ritz and Streibig, J. Stat. Software 12 (2005), 1-22). The model has the following form:

$$f(x, (b, d, e)) = \frac{d}{1 + \exp\{b(\log(x) - \log(e))\}}$$

In the above formula, x is the drug concentration, e is the response half-way between the upper limit d and 0, and b is the relative slope around e. From the estimated dose response curve, the response value (IL6 or IL8 levels) was determined at the highest tested drug dosage (IL6max or IL8max). Data on the expression of IL6 and IL8 in three batches of HPTC had been obtained previously (Li et al., Toxicol. Res. 2 (2013), 352-362) and were re-analyzed here.

A support vector machine (SVM) (Cortes, C. and Vapnik, V., Machine Learning 20 (1995), 273-297) with radial basis function kernel was used to predict drug induced nephrotoxicity. The SVM has two parameters: the regularization/cost parameter (C) and the width of the radial basis function kernel ($\gamma$). These parameters were optimized using an exhaustive grid search (C.-W. Hsu, Chang and C.-J. Lin, A practical guide to support vector classification. National Taiwan University, 2003) for C=10-5 to 105, and β=10-5 to 105.

Finally, a 3-fold cross validation procedure was used to estimate classification performance (Hastie et al. (eds) The Elements of Statistical Learning: Data Mining, Inference, and Prediction, $2^{nd}$ Ed, (2009), Springer Science+Business Media LLC, Philadelphia, Pa., USA).

Whole datasets were randomly divided into three roughly equal and stratified folds, two of which were used to train the SVM and the remaining fold to test the trained SVM. The whole procedure was repeated 10 times. All the classification performance measurements were averaged from these 10 trials. The following three classification performance measurements were used:

$$Sensitivity = TP/TP + FN \times 100\%$$

$$Specificity = TN/TN + FP \times 100\%$$

$$Balanced\ accuracy = sensitivity + specificity/2 \times 100\%$$

TP is the number of true positives, TN is the number of true negatives, FP is the number of false positives and FN is the number of false negatives. All the analyses were performed using the 'e1071' library (v1.6-1) under the R statistical environment (v3.0.2) on a personal computer equipped with an Intel Core i7-3770K processor and Windows 7 operating system.

Figure 3:
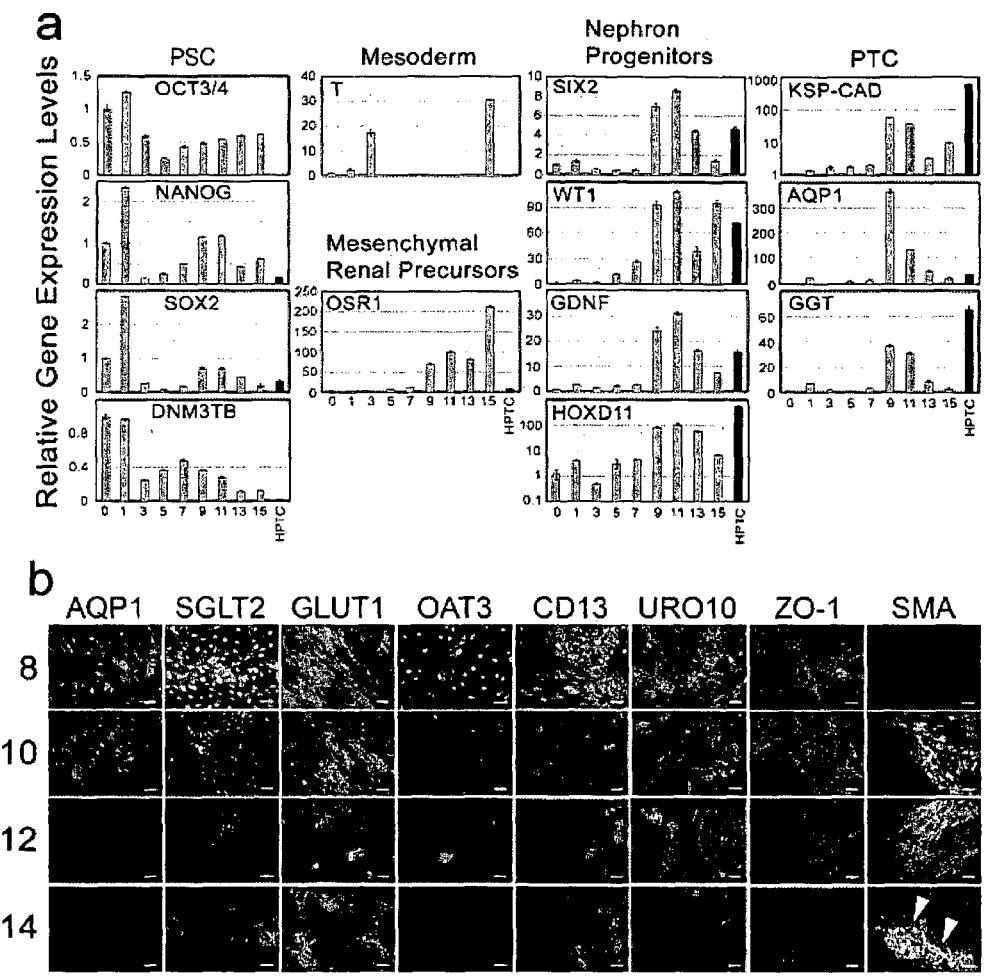
FIG. 3. Changes of marker expression patterns of iPS (Foreskin)-4-derived cells during differentiation.

FIG. 3. Changes of Marker Expression Patterns of iPS (Foreskin)-4-Derived Cells During Differentiation.

a) Marker expression levels were determined by qPCR on every other day during a time period of 15 days (gray bars). The differentiation protocol was applied on day 1. The bars show the mean+/−standard deviation (s.d., n=3). Marker expression levels were normalized to the expression levels of the respective marker in undifferentiated iPS(Foreskin)-4 cells (day 0). Mean expression levels in undifferentiated hiPSC were set to 1. Black bars indicate expression levels in HPTC (in some cases expression levels were very low and the bar is not visible). The markers examined are indicated, as well as their in vivo expression patterns (PSC, mesoderm, mesenchymal renal precursors, nephron progenitors, PTC). All gene IDs, descriptions and acronyms of markers examined by qPCR are summarized in the Table 1. b) PTC-specific markers were detected on day 8, 10, 12 and 14 by immunostaining (green; cell nuclei: blue). The following markers were detected: AQP1, solute carrier family 5 (sodium/glucose cotransporter), member 2 (SGLT2), solute carrier family 2 (facilitated glucose transporter), member 1 (GLUT)1, organic anion transporter (OAT)3, alanyl (membrane) aminopeptidase (CD13), urothelial glycoprotein (URO)10, zonula occludens (ZO)-1 and (smooth muscle actin (SMA). A cell aggregate expressing high levels of SMA is marked by arrowheads. Scale bars: 50 μm.

Figure 4:
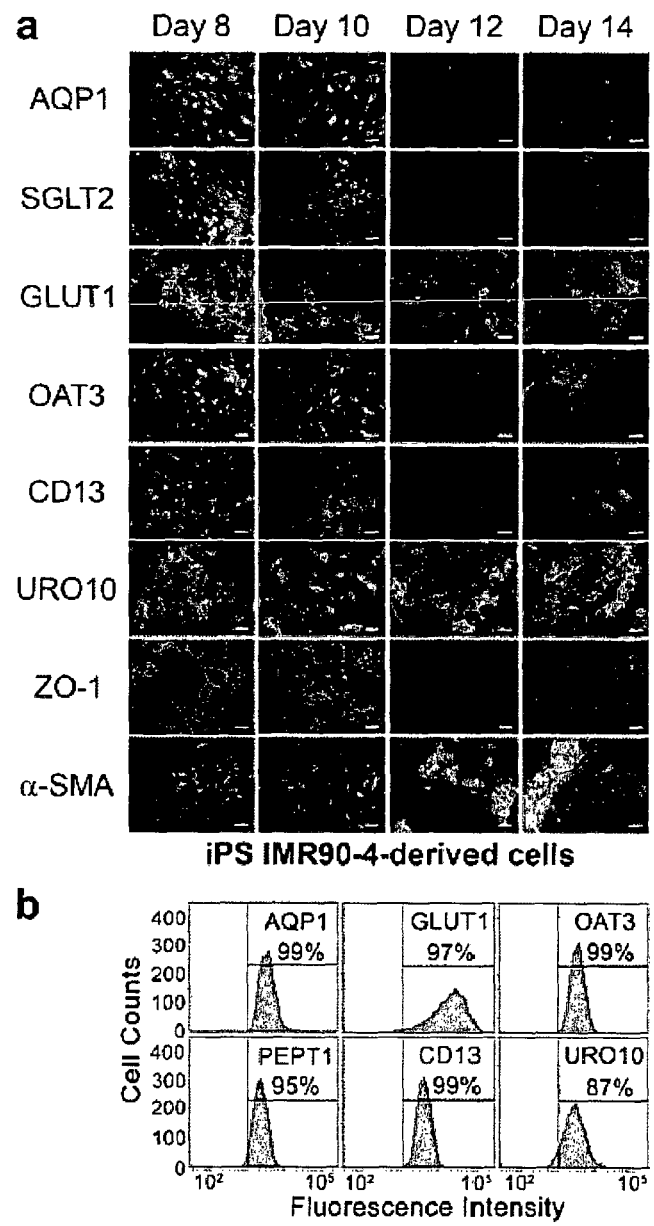
FIG. 4. Marker protein expression of iPS IMR90-4- and iPS DF19-9-11T.H-derived cells.

FIG. 4. Marker Protein Expression of iPS IMR90-4- and iPS DF19-9-11T.H-Derived Cells.

a) iPS IMR90-4 cells were differentiated for various time periods. The results obtained with cells tested on day'8, 10, 12 and 14 are shown. The markers detected by immunofluorescence (green) are indicated on the left. Cell nuclei are displayed in blue. The expression of most PTC markers declined after day 10. Cell aggregates that were intensely stained for αSMA (arrowheads) occurred at later time points. Scale bars: 50 μm. b) FACS results obtained With iPS DF19-9-11T.H-derived d8 cells. The percentages of cells positive for the markers indicated are displayed.

Figure 5:
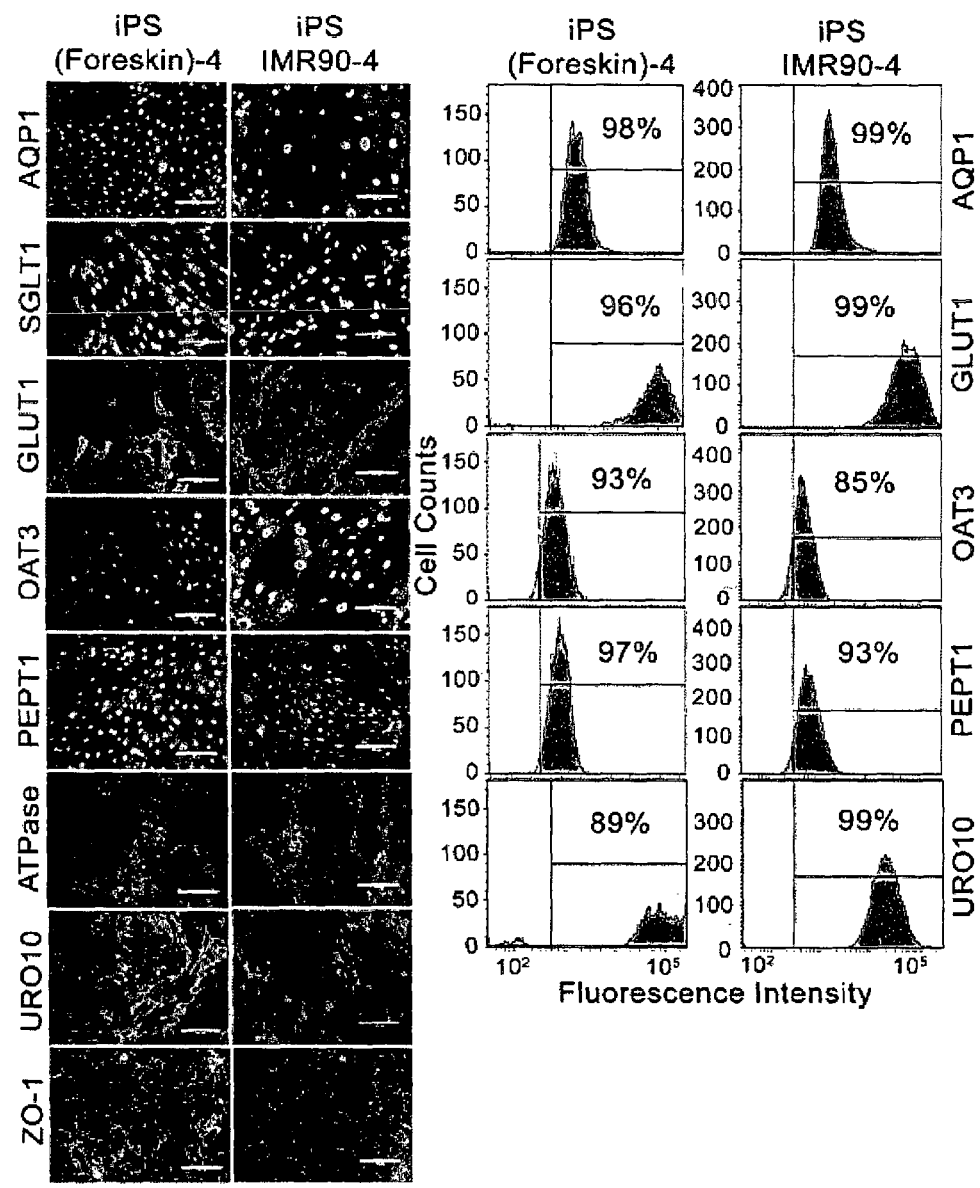
FIG. 5. Characterization of hiPSC-derived d8 cells by immunostaining and FACS.

FIG. 5. Characterization of hiPSC-Derived d8 Cells by Immunostaining and FACS.

The left-hand panels show epithelia of d8 cells derived from iPS(Foreskin)-4 and iPS IMR90-4 cells. The PTC-specific markers indicated on the left were detected by immunofluorescence (green; cell nuclei: blue): Scale bars: 100 μm. The right-hand panels show FACS results obtained with iPS(Foreskin)-4-, or iPS IMR90-4-derived d8 cells. The percentages of cells positive for the markers indicated on the right are displayed. The FACS results were consistent with the immunostaining data and showed that in most cases >90% of the cells were positive.

Figure 6:
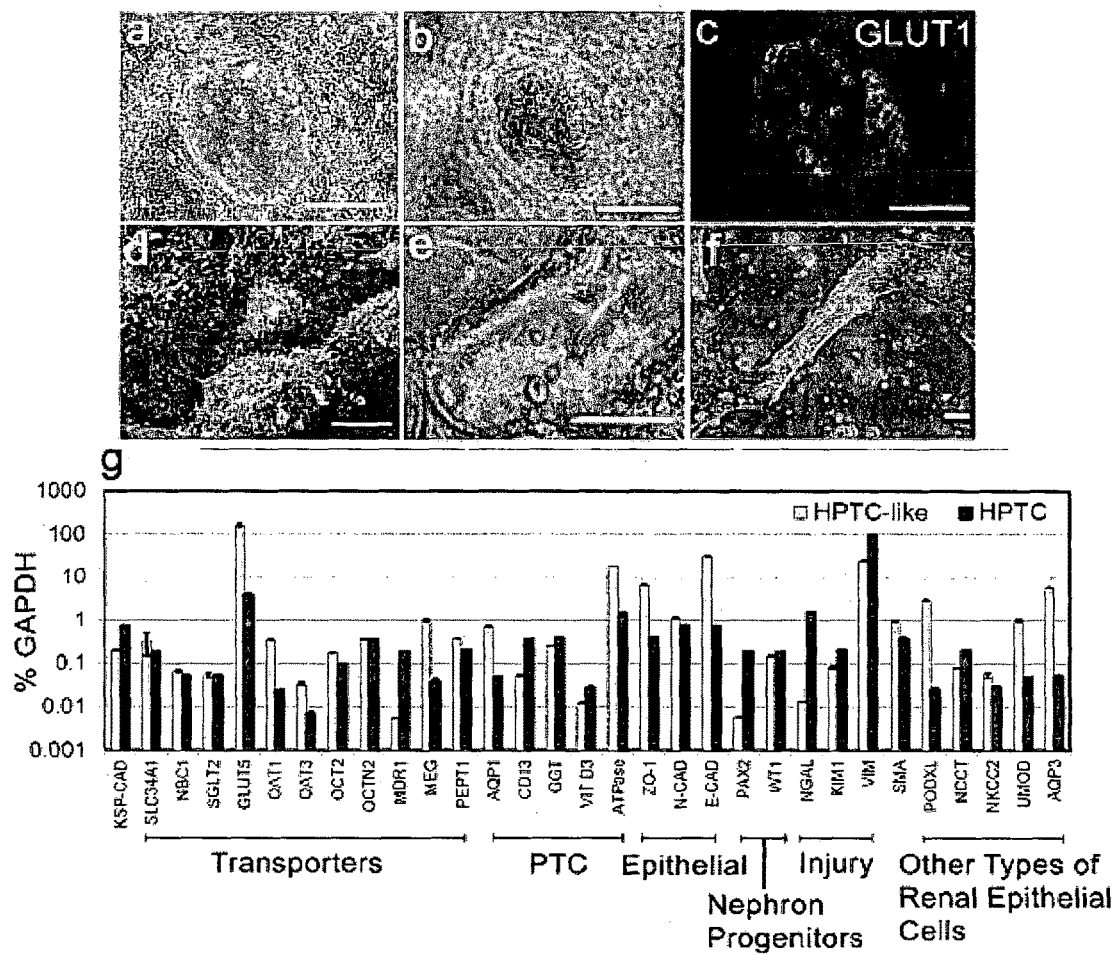
FIG. 6. Characterization of iPS(Foreskin)-4-derived d8 cells.

FIG. 6. Characterization of iPS(Foreskin)-4-Derived d8 Cells.

a-c) Dome formed by cells cultivated on tissue culture plastic (TCPS). Different focal planes are displayed in panels a) and b). c) GLUT1 (green) was detected by immunofluorescence. Scale bars: 100 μm. d) Cells were polarized with an apical brush border (scale bar: 5 μm). Tubules generated by cells cultivated on the surface of Matrigel (e) or TCPS (f). Scale bars: 100 μm. g) The expression levels of 31 markers were determined by qPCR in iPS(Foreskin)-4-derived HPTC-like d8 cells (gray bars) and HPTC (black bars). The bars show the means+/−s.d. (n=3). Markers were grouped according to their functions or in vivo expression patterns as indicated at the bottom.

Figure 7:
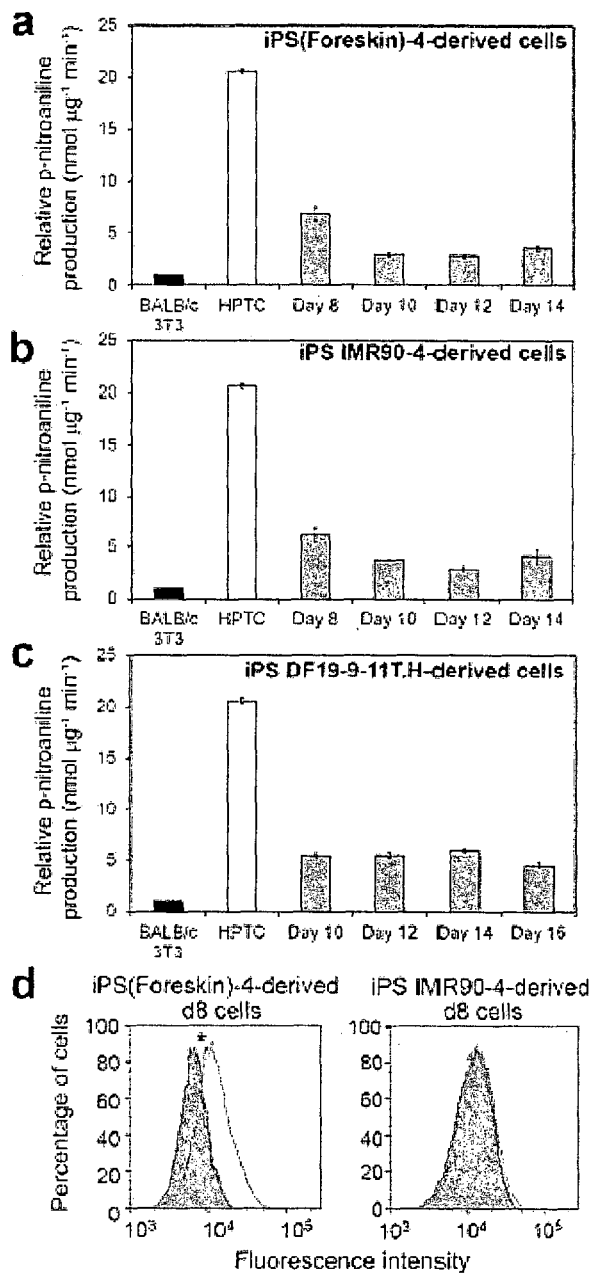
FIG. 7. GGT activity and OCT2 activity of hiPSC-derived cells.

FIG. 7. GGT Activity and OCT2 Activity of hiPSC-Derived Cells.

a-c) Relative GGT activity was determined in BALB/c 3T3 fibroblasts (negative control, black bars), HPTC (positive control, white bars) and hiPSC-derived cells (grey bars). hiPSC-derived were tested at different time points as indicated on the x-axis. The bars show the mean+/−standard deviation (s.d., n=3). All results were normalized to the results obtained with BALB/c 3T3 cells, which were set to 1. Results obtained with iPS(Foreskin)-4- (panel a), iPS IMR90-4- (panel b) and iPS DF19-9-11T.H-derived cells (panel c) are shown. d) OCT2 activity of hiPSC-derived cells. iPS(Foreskin)-4- and iPS IMR90-4-derived d8 cells were incubated with vehicle (DMSO)-containing cell culture medium, or with cell culture medium containing 50 μm of the OCT2 inhibitor tetrapentylammonium. After incubation for 5 minutes, 25 μm of the fluorescent OCT2 substrate $ASP^+$ (4-(4-(dimethylamino)styryl)-N-methylpyridinium iodide) were added. After 30 minutes propidium iodide was added for monitoring cell viability and the cells were analysed by FACS. The diagrams show the cellular fluorescence intensities (n=3) of inhibitor-treated samples (gray) and vehicle controls (white). Both graphs overlap to a large extent in case of iPS IMR90-4-derived cells, which shows that there is no difference between OCT2 inhibitor-treated samples and vehicle controls. This indicates lack of OCT2 activity in these cells. In case of iPS(Foreskin)-4-derived cells inhibitor-treated cells displayed decreased fluorescence intensity, consistent with decreased uptake of the fluorescent OCT2 substrate in the presence of the OCT2 inhibitor. Data analysis yielded an MDR activity factor (MAF) value >25. Samples with MAF values >25 are considered as being positive for transporter activity (asterisk).

Figure 8:
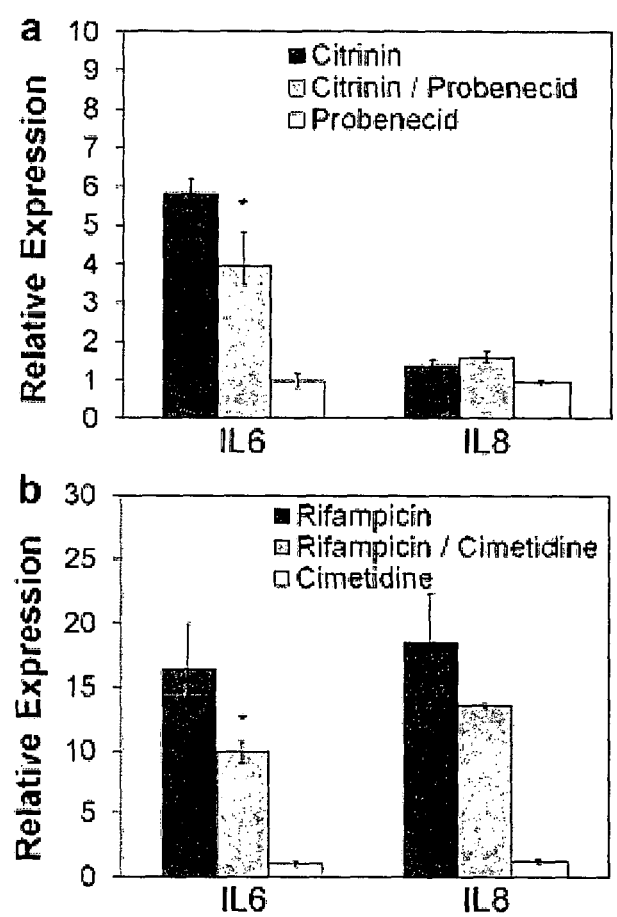
FIG. 8. Transporter-mediated drug uptake and drug-induced expression of IL6 and IL8.

FIG. 8. Transporter-Mediated Drug Uptake and Drug-Induced Expression of IL6 and IL8.

iPS(Foreskin)-4-derived d8 HPTC-like cells were treated with 100 μg/ml of (a) citrinin or (b) rifampicin. IL6 and IL8 expression levels in drug-treated cells are indicated by the dark gray bars. The bars show the mean+/−s.d. (n=3) and all expression levels were normalized to the vehicle controls, which were set to 1. Citrinin uptake by PTC is mediated by OAT1 and OAT3 and these transporters are inhibited by probenecid. Exposure to citrinin and probenecid (light-gray bars in panel a) reduced the levels of citrinin-induced IL6 expression by 31%. Rifampicin uptake by PTC is mediated by OCT2, which is inhibited by cimetidine. Exposure to rifampicin and cimetidine reduced the levels of rifampicin-induced IL6 and IL8 expression by 40% and 26%, respectively (light-gray bars in panel b). The inhibitors alone did not significantly alter IL6 and IL8 expression levels relative to Vehicle controls (white bars; both inhibitors were used at a concentration of 2 mM). Significant differences between drug treated and drug+inhibitor-treated samples are indicated by asterisks.

Figure 9:
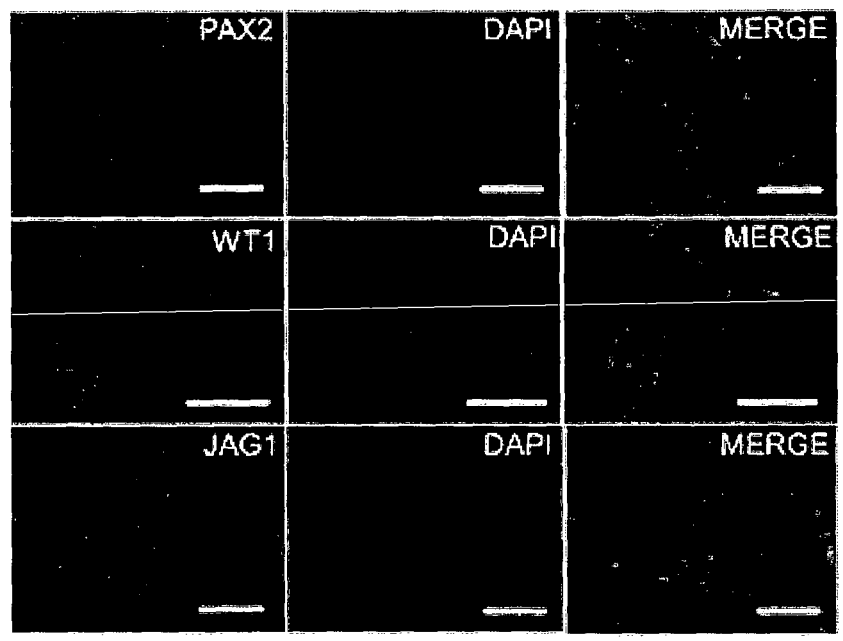
FIG. 9. Marker expression in hiPSC-derived cells.
Figure 9:
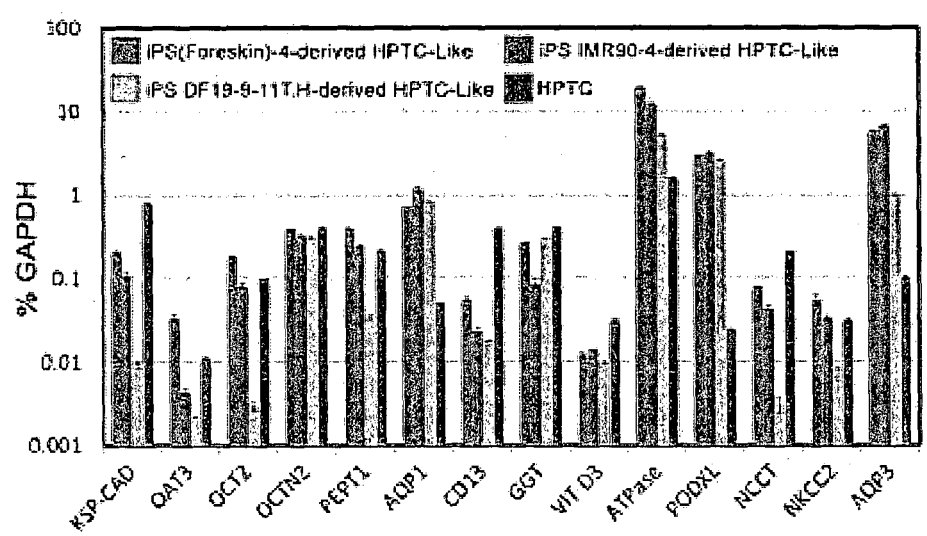

FIG. 9. Marker Expression in hiPSC-Derived Cells.

PAX2, WT1 and JAG1 were detected by immunofluorescence (red; left-hand panels) in iPS(Foreskin)-4-derived d8 cells. 4',6-diamidino-2-phenylindole (DAPI)-stained cell nuclei are shown in blue (middle). The right-hand panels show the merges. Scale bars: 200 μm. b) The expression levels of the 14 markers indicated on the x-axis were determined by qPCR in hiPSC-derived d8 cells and HPTC. The cell types are represented by the different colors as indicated. All expression levels are displayed as % of GAPDH expression. The bars show the mean+/−s.d. (n=3).

Figure 10:
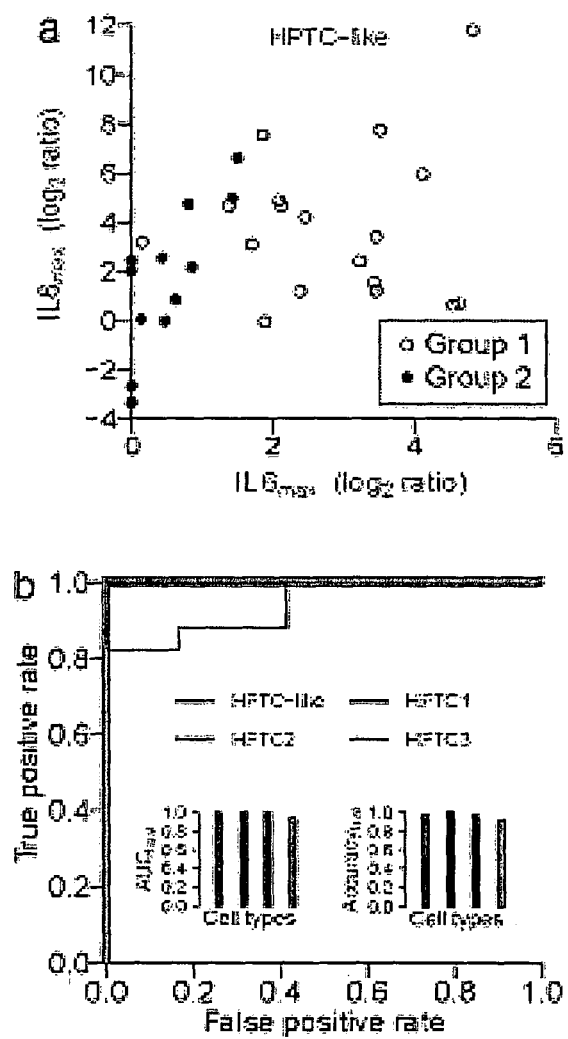
FIG. 10. Predictive performances of HPTC and iPSC-derived HPTC-like cells.

FIG. 10. Prediction Performances of HPTC and HPTC-Like Cells.

a) Scatter plot showing changes in the IL6 and IL8 gene expression levels of HTPC-like cells induced by Group 1 (white; toxic for PTC in humans) and Group 2 (black; not toxic for PTC in humans) compounds. Each dot represents a compound. These features were used to train a Support Vector Machine (SVM) classifier. b) The receiver operating characteristic (ROC) curves of the final SVMs trained on all data collected from HPTC-like cells (red), and three batches of HPTC (HPTC1—blue, HPTC2—purple, and HPTC 3—green). The red, blue and purple graphs overlap. The insets provide the values for the area under the curve ($AUC_{final}$) and balanced accuracy ($Accuracy_{final}$) of the classifiers. SVM based on the HPTC-like cells and HPTC batches 1 and 2 can perfectly separate the 30 compounds.

Results

Gene and Protein Expression During Differentiation:

Three well-characterized hiPSC lines, iPS(Foreskin)-4, iPS IMR90-4 and iPS DF19-9-11T.H, were differentiated with the protocol described in the Materials and Methods section (Expansion and differentiation of hiPSC). Changes in gene expression patterns were monitored in iPS(Foreskin)-4-derived cells over a period of 15 days (FIG. 3a). OCT3/4, NANOG, SOX2 and DNMT3B were down-regulated after day (d) 1. Down-regulation of these "stemness" markers was followed by a transient pulse of T on d3 (FIG. 3a). T is transiently expressed in the early, mesoderm of vertebrate embryos, from which the kidneys are derived. Down-regulation of "stemness" markers and an early transient pulse of T has typically been observed when pluripotent stem cells (PSC) are differentiated towards the renal lineage.

Here, T was expressed again at low levels on days 5-13. OSR1 became strongly up-regulated between d7 and d9 (FIG. 3a). During embryonic development OSR1 is continuously expressed throughout development in the renal precursor population 15. Between d7 and d9 also nephron progenitor and PTC markers became strongly up-regulated (FIG. 3a). These included the nephron progenitor markers SIX2, WT1 and GDNF, as well as HOXD11, which specifies metanephric kidney development. PTC markers that were up-regulated between d7 and d9 were KSP-CAD, AQP1 and GGT. The expression of KSP-CAD is kidney-specific, and limited to tubular epithelial cells. AQP1 and GGT expression is characteristic for proximal tubular epithelial cells.

These results showed a profound change between d7 and d9, and on d9 the cells expressed high levels of all nephron progenitor and PTC markers tested. Although nephron progenitor markers are not expressed in mature human PTC in vivo, they become typically re-expressed under in vitro conditions. This was confirmed by the results obtained here showing that in vitro cultures of HPTC isolated from adult human kidneys (FIG. 3a; black bars) expressed a similar pattern of nephron progenitor and PTC markers as hiPSC-derived cells on d9. Immunostaining revealed that cells derived from all three hiPSC lines formed a confluent epithelium with tight junctions and proper PTC-specific protein expression and localization on d8 (FIG. 3b, FIGS. 4a and 5):

The changes in gene expression observed here, which included early down-regulation of stemness markers, a transient peak of T and subsequent up-regulation of OSR1 and nephron progenitor markers, were in agreement with the results of recent previous studies that applied multistep protocols for the differentiation of PSC towards the renal lineage. In most of those studies, also up-regulation of markers expressed in terminally differentiated renal cells was observed, as was the case here.

Here, a progressive decline in the expression of PTC-specific marker genes was observed after d9, and a decline in the expression of nephron progenitor markers after d11 (FIG. 3a). These qPCR results were consistent with immunostaining results showing a decline in the expression of PTC and epithelial markers proteins on (iPS DF19-9-11 T.H-derived cells) or after (iPS(Foreskin)-4- and iPS IMR90-4-derived cells) d10 (FIG. 3b and FIG. 4).

Whereas PTC and epithelial markers were down-regulated at later time points and were expressed at relatively low levels on d15 (except WT1), the mesodermal and mesenchymal markers T and OSR1 were strongly up-regulated at this time point (FIG. 3a). Also, the myofibroblast marker SMA was expressed at increasing levels in cell aggregates at later time points (FIG. 3b and FIG. 4). Similar processes have been observed previously when HPTC were cultivated in vitro for extended time periods and up-regulation of SMA was associated with epithelial-mesenchymal transition (EMT) of PTC. T has been implicated to play a key role in EMT. The up-regulation of T, OSR1 and SMA at later time points (FIG. 3) would be consistent with EMT occurring also in hiPSC-derived HPTC-like cells (as in HPTC) when cultivated for extended time periods. It is important to note that also terminally differentiated proximal tubular cells maintain a high degree of flexibility and can easily switch between epithelial and mesenchymal states; this flexibility seems to be associated with their role in tissue regeneration.

Characterization of hiPSC-Derived d8 Cells:

d8 cells were further examined, as the results revealed that hiPSC-derived cells up-regulated typical FTC-specific marker genes between d7 and d9 (FIG. 3a), and formed confluent epithelia and expressed PTC-specific patterns of marker proteins on d8 (FIG. 3b and FIG. 4). Immunostaining experiments repeated with independently derived batches of differentiated cells confirmed that on d8 iPS(Foreskin)-4- and iPS IMR90-4-derived cells formed confluent renal epithelia (FIG. 5). Almost all cells expressed PTC specific marker proteins, including AQP1, Na+/K+ ATPase, OAT3, PEPT1, SGLT1, GLUT1; URO10 and ZO-1 (FIG. 5). FACS experiments revealed that marker proteins were expressed in more than 90% of the cells in most cases, and this applied to cells derived from all three hiPSC lines (FIGS. 4 and 5). Therefore, further purification of these cells for in vitro applications would not be required.

iPS(Foreskin)-4-derived d8 cells had typical morphological and functional characteristics of HPTC and displayed dome formation, polarization with an apical brush border and tubulogenesis (FIG. 6a-f; similar processes of tubulogenesis on Matrigel and tissue culture plastic have been observed with HPTC and hESC-derived HPTC-like cells). Further, cells derived from all three hiPSC lines displayed GGT activity, although hiPSC-derived cells had less GGT activity than HPTC (FIG. 7). Consistent with the other results (FIG. 3) GGT activity declined at later time points in iPS(Foreskin)-4- and iPS IMR90-4-derived cells. When d8 cells derived from these two hiPSC lines were tested for transporter activity it turned out that efflux transporters (MDR1, MRP2, BCRP) were inactive in both cases. However, the organic cation uptake transporter OCT2 was active in iPS(Foreskin)-4-derived d8 cells (FIG. 7d), and the organic anion uptake transporter OAT3 was expressed in a high percentage of such cells (FIG. 5). Therefore, iPS (Foreskin)-4-derived cells were selected for further characterization.

Marker expression patterns of iPS(Foreskin)-4-derived d8 cells were characterized in detail by qPCR, and the expression levels of 31 markers were determined in another independently differentiated batch of such HPTC-like cells and in HPTC (FIG. 6g). The results confirmed that KSP-CAD was expressed in both cell types, as well as SLC34A1. This gene codes for a type II sodium/phosphate cotransporter, which is expressed only in fully differentiated PTC. Also other PTC-specific transporters were expressed, which are involved in sodium, bicarbonate and glucose transport (NBC1, SGLT2 and GLUT5). In addition, all drug transporters tested were expressed. The expression levels of the main organic anion uptake transporters, OAT1 and OAT3, were ~15-fold (P=0.0004) or ~5-fold (P=0.0157) higher in HPTC-like cells, respectively (compared to HPTC). About 2-fold higher expression levels were observed in case of OCT2 (P=0.0005), which is important for uptake of various nephrotoxicants by PTC, including cisplatin. PEPT1 and MEG were expressed at ~2-fold (P=0.0001) and ~26-fold (P=0.0041) higher levels HPTC-like cells. MEG is important for the uptake of nephrotoxic aminoglycoside antibiotics. The organic cation uptake transporter OCTN2 was expressed at similar levels in both cell types (P=0.1608) and the efflux transporter MDR1 was expressed at higher levels in HPTC (~39-fold; P=0.0003). This was in agreement with the observation that efflux transporters had no detectable activity in iPS(Foreskin)-4-derived HPTC-like cells, in contrast to uptake transporters (FIGS. 7 and 8).

Consistent with the other results, also a variety of other PTC-specific markers (AQP1, CD13, GGT, VIT D3, Na+K+ ATPase) were expressed in this batch of iPS(Foreskin)-4-derived HPTC-like cells and in HPTC, as well as epithelial markers (ZO-1, N-CAD, E-CAD; FIG. 6g). PAX2 and WT1 were expressed as well. These two markers are expressed in renal and nephron progenitors and HPTC cultivated in vitro. Expression of PAX2, WT1 and the renal vesicle marker JAG131 was confirmed by immunostaining (FIG. 9). In addition, expression of kidney injury markers (NGAL, KIM-1, VIM) and SMA was observed (FIG. 6g). Also expression of kidney injury-markers, as well as of E-CAD and SMA (increasing over time), occurs in PTC under in vitro conditions. Of note, PAX2 and NGAL were expressed at about 34-(P=0.00003) or 122-fold (P=0.0002) lower levels in HPTC-like cells, respectively, and also KIM-1 and VIM were expressed at about 3-(P=0.0002) to 4-fold (P=2.4×10-7) lower levels in this cell type (compared to HPTC).

Both cell types also expressed markers that are under in vivo conditions specific for other renal epithelial cell types: PODXL (podocytes), NCCT (distal tubule), NKCC2 (thick ascending limb of Henle's loop), UMOD (Tamm-Horsfall glycoprotein, thick ascending limb of Henle's loop) and AQP3 (collecting duct; FIG. 6g). Also this usually occurs under in vitro conditions and has been previously observed in HPTC and hESC-derived HPTC-like cells. Here, it was confirmed by immunostaining that the PTC marker AQP1 and the collecting duct marker AQP3 were co-expressed by the same cells (data not shown). Therefore, mixed marker expression patterns were not due to the presence of different cell populations. This is consistent with the fact that in most cases >90% of cells expressed PTC-specific markers (FIG. 5).

For comparison, expression levels of 14 selected markers were determined also in iPS IMR90-4- and iPS DF19-9-11T.H-derived d8 cells and the results for d8 cells derived from all three hiPSC-lines and HPTC are displayed in the FIG. 9. The results showed that all markers were expressed by all four cell types. iPS(Foreskin)-4-derived cells displayed the highest expression levels in most cases.

Drug Uptake and Drug-Induced Interleukin Expression:

Compounds that are toxic for PTC specifically increase IL6 and/or IL8 expression in HPTC and hESC-derived HPTC-like cells. Based on this characteristic increase of IL6/IL8 expression a method was previously developed for the prediction of PTC toxicity in humans. Here, it was tested whether compounds that are toxic for PTC increase IL6 and/or IL8 expression in iPS(Foreskin)-4-derived d8 cells. The cells were differentiated as usual in multi-well plates, and were treated on the evening of day 8 for 16 hours with the PTC-specific nephrotoxicants citrinin and rifampicin. IL6 and IL8 levels were determined subsequently by qPCR (a flow chart of the procedures is provided in FIG. 1). Rifampicin increased IL6 expression ~17-fold and IL8 expression ~18-fold (FIG. 8). Citrinin increased IL6 expression ~6-fold, whereas no increase in IL8 expression was observed (FIG. 8). Previous results revealed that citrinin also did not induce IL8 in hESC-derived HPTC-like cells, and typically not every drug induces both interleukins.

Citrinin uptake by PTC is mediated by OAT1 and OAT3. These transporters are inhibited by probenecid. Co-incubation with citrinin and probenecid reduced the level of citrinin induced IL6 expression significantly by ~31% (FIG. 8). This result revealed that citrinin uptake was mediated by OAT1 and OAT3, in agreement with the expression of these transporters in iPS(Foreskin)-4-derived d8 cells (FIGS. 5 and 6g).

Similar experiments were performed with rifampicin. Uptake of this drug by PTC is mediated by OCT2, which is inhibited by cimetidine. Co-incubation with cimetidine reduced the rifampicin-induced increase of IL6 and IL8 expression by 40% and 26%, respectively (FIG. 8). These results suggested that rifampicin-induced induction of IL6 and IL8 was dependent on transporter-mediated uptake of the drug. The results were in agreement with expression (FIG. 6g) and activity (FIG. 7) of ~OCT2 in iPS(Foreskin)-4-derived d8 cells.

Predictive Performance:

Next, it was addressed whether PTC-specific nephrotoxicity of drugs could be predicted with hiPSC-derived HPTC-like cells. This question was addressed with the IL6/IL8-based assay (for overall procedure see FIG. 1). Briefly, iPS(Foreskin)-4-derived d8 cells were exposed overnight to 30 compounds (Tables 2 and 3). These could be divided into two groups. Group 1 contained 18 nephrotoxicants that are directly toxic for PTC in humans (Tables 2 and 3). Group 2 contained compounds that are not toxic for PTC in humans. This group comprised 4 non-nephrotoxic compounds and 8 nephrotoxicants that do not directly damage PTC (Tables 2 and 3). All compounds, except of the PTC-damaging compound aristolochic acid, were used in previously reported studies and detailed information on the nephrotoxicity of the compounds in humans has been provided (Li et al., Toxicol. Res. 2 (2013), 352-362; Li et al. Mol. Pharm. 11 (2014), 1982-1990). After overnight exposure, changes in the levels of IL6 and IL8 were determined by qPCR. Tables 2 and 3 show the results on IL6 and IL8 expression levels for all 30 compounds at all concentrations tested. All compounds were blinded during testing.

TABLE 2

Compound-induced IL6 expression in iPS(foreskin)-4-derived d8 cells.

| | Compound | \multicolumn{5}{c}{IL6 Expression Levels} | | | | |
| --- | --- | --- | --- | --- | --- | --- |
| | | 0 | 1 | 10 | 100 | 1,000 |
| 1 | Aristolochic acid | 1.0 ± 0.0 | 3.9 ± 0.5 | 3.3 ± 0.2 | 7.3 ± 1.6 | 9.3 ± 0.5 |
| 2 | Arsenic (III) oxide | 1.0 ± 0.1 | 1.5 ± 0.1 | 5.2 ± 0.1 | 14.2 ± 2.1 | 8.2 ± 0.3 |
| 3 | Bismuth (III) oxide | 1.0 ± 0.2 | 1.2 ± 0.1 | 1.3 ± 0.2 | 2.1 ± 0.1 | 3.6 ± 0.3 |
| 4 | Cadmium chloride | 1.1 ± 0.1 | 3.6 ± 0.4 | 10.9 ± 0.4 | 10.3 ± 1.6 | 11.8 ± 0.5 |
| 5 | Cephalosporin C | 1.0 ± 0.0 | 1.6 ± 0.2 | 1.7 ± 0.2 | 9.8 ± 2.2 | 24.3 ± 1.6 |
| 6 | Cisplatin | 1.0 ± 0.1 | 6.0 ± 0.8 | 5.5 ± 1.0 | 3.9 ± 0.3 | ND |
| 7 | Citrinin | 1.0 ± 0.1 | 4.1 ± 0.1 | 9.2 ± 0.3 | 24.5 ± 3.0 | 5.4 ± 0.1 |
| 8 | Copper (II) chloride | 1.0 ± 0.1 | 1.2 ± 0.1 | 2.2 ± 0.2 | 22.5 ± 2.2 | 13.4 ± 0.0 |
| 9 | 5-Fluorouracil | 1.0 ± 0.0 | 6.2 ± 0.7 | 6.4 ± 0.3 | 9.2 ± 1.2 | 1.1 ± 0.2 |
| 10 | Gentamicin | 1.0 ± 0.1 | 1.6 ± 0.3 | 1.7 ± 0.3 | 2.3 ± 0.3 | 12.1 ± 0.4 |
| 11 | Gold (I) chloride | 1.0 ± 0.1 | 1.2 ± 0.2 | 1.2 ± 0.1 | 2.9 ± 0.2 | 23.3 ± 0.4 |
| 12 | Lead acetate | 1.0 ± 0.1 | 1.3 ± 0.3 | 1.2 ± 0.3 | 1.5 ± 0.1 | 4.3 ± 0.8 |
| 13 | Paraquat | 1.0 ± 0.0 | 1.6 ± 0.2 | 1.8 ± 0.2 | 5.4 ± 0.6 | 3.5 ± 0.3 |
| 14 | Potassium dichromate | 1.0 ± 0.1 | 1.2 ± 0.4 | 1.0 ± 0.0 | 3.3 ± 0.3 | 3.7 ± 0.4 |
| 15 | Puromycin | 1.0 ± 0.1 | 1.9 ± 0.2 | 14.1 ± 1.2 | 29.0 ± 1.2 | 26.6 ± 4.3 |
| 16 | Rifampicin | 1.0 ± 0.1 | 5.8 ± 0.9 | 4.5 ± 0.3 | 2.3 ± 0.2 | 9.3 ± 0.6 |
| 17 | Tacrolimus | 1.0 ± 0.1 | 6.6 ± 0.6 | 6.1 ± 0.2 | ND | ND |
| 18 | Tobramycin | 1.0 ± 0.1 | 1.3 ± 0.1 | 1.3 ± 0.1 | 1.4 ± 0.1 | 2.7 ± 0.4 |
| 19 | Acetaminophen | 1.0 ± 0.1 | 1.3 ± 0.0 | 1.2 ± 0.1 | 1.4 ± 0.2 | 0.3 ± 0.1 |
| 20 | Ethylene glycol | 1.0 ± 0.1 | 1.2 ± 0.1 | 1.1 ± 0.2 | 1.2 ± 0.1 | 1.6 ± 0.2 |
| 21 | Lincomycin | 1.0 ± 0.0 | 1.2 ± 0.1 | 1.3 ± 0.1 | 1.2 ± 0.1 | 1.4 ± 0.2 |
| 22 | Lindane | 1.0 ± 0.0 | 7.3 ± 1.7 | 6.4 ± 0.5 | 5.1 ± 0.4 | 0.8 ± 0.0 |
| 23 | Lithium chloride | 1.0 ± 0.1 | 1.2 ± 0.0 | 1.1 ± 0.1 | 1.2 ± 0.1 | 1.8 ± 0.1 |
| 24 | Phenacetin | 1.0 ± 0.0 | 7.2 ± 0.2 | 7.0 ± 1.1 | 5.3 ± 0.1 | 0.7 ± 0.2 |
| 25 | Valacyclovir | 1.0 ± 0.1 | 1.3 ± 0.1 | 1.3 ± 0.1 | 1.6 ± 0.1 | 2.8 ± 0.4 |
| 26 | Vancomycin | 1.0 ± 0.1 | 1.5 ± 0.3 | 1.4 ± 0.1 | 1.4 ± 0.1 | 3.1 ± 0.2 |
| 27 | Acarbose | 1.0 ± 0.0 | 1.2 ± 0.1 | 1.5 ± 0.3 | 1.3 ± 0.2 | 1.4 ± 0.4 |
| 28 | Glycine | 1.0 ± 0.3 | 1.6 ± 0.1 | 1.9 ± 0.3 | 1.7 ± 0.2 | 1.9 ± 0.2 |
| 29 | Melatonin | 1.0 ± 0.1 | 6.5 ± 0.8 | 6.1 ± 0.4 | 4.4 ± 0.4 | 1.1 ± 0.1 |
| 30 | Ribavirin | 1.0 ± 0.1 | 1.4 ± 0.1 | 1.5 ± 0.1 | 1.2 ± 0.3 | 1.0 ± 0.1 |

TABLE 3

Compound-induced IL8 expression in iPS(foreskin)-4-derived d8 cells.

| | Compound | \multicolumn{5}{c}{IL8 Expression Levels} | | | | |
| --- | --- | --- | --- | --- | --- | --- |
| | | 0 | 1 | 10 | 100 | 1,000 |
| 1 | Aristolochic acid | 1.0 ± 0.3 | 5.0 ± 0.8 | 4.8 ± 0.6 | 43.5 ± 7.2 | 1.6 ± 0.9 |
| 2 | Arsenic (III) oxide | 1.0 ± 0.1 | 1.2 ± 0.5 | 4.2 ± 0.1 | 1.5 ± 0.2 | 3.9 ± 1.6 |
| 3 | Bismuth (III) oxide | 1.0 ± 0.2 | 0.4 ± 0.1 | 2.6 ± 0.2 | 33.0 ± 1.6 | 192.7 ± 18.4 |
| 4 | Cadmium chloride | 1.1 ± 0.3 | 15.0 ± 0.8 | 7.6 ± 0.4 | 4.4 ± 0.6 | 20.5 ± 8.3 |
| 5 | Cephalosporin C | 1.0 ± 0.1 | 1.0 ± 0.1 | 0.7 ± 0.1 | 1.5 ± 0.9 | ND |
| 6 | Cisplatin | 1.0 ± 0.0 | 3.0 ± 1.8 | 3.3 ± 1.1 | 5.8 ± 1.0 | ND |
| 7 | Citrinin | 0.9 ± 0.0 | 2.2 ± 0.2 | 1.3 ± 0.5 | 2.5 ± 0.3 | ND |
| 8 | Copper (II) chloride | 1.0 ± 0.2 | 7.2 ± 0.6 | 67.1 ± 18.1 | 58.2 ± 3.2 | ND |
| 9 | 5-Fluorouracil | 1.0 ± 0.1 | 7.4 ± 1.4 | 9.2 ± 1.4 | 18.3 ± 2.2 | 5.7 ± 0.5 |
| 10 | Gentamicin | 1.0 ± 0.2 | 0.7 ± 0.3 | 0.6 ± 0.1 | 2.2 ± 0.5 | 216.2 ± 16.2 |
| 11 | Gold (1) chloride | 1.0 ± 0.2 | 0.9 ± 0.2 | 0.9 ± 0.1 | 2.0 ± 0.0 | 1.2 ± 0.2 |
| 12 | Lead acetate | 1.0 ± 0.1 | 0.4 ± 0.2 | 1.3 ± 0.1 | 5.0 ± 0.8 | 29.4 ± 5.1 |
| 13 | Paraquat | 1.0 ± 0.3 | 0.7 ± 0.2 | 1.5 ± 0.3 | 2.9 ± 0.4 | 25.5 ± 8.5 |
| 14 | Potassium, dichromate | 1.0 ± 0.1 | 0.5 ± 0.0 | 0.7 ± 0.1 | 0.8 ± 0.0 | 1.2 ± 0.0 |
| 15 | Puromycin | 1.0 ± 0.3 | 0.8 ± 0.2 | 255.7 ± 28.2 | 3,284.1 ± 1,069.3 | 3,852.3 ± 309.9 |
| 16 | Rifampicin | 1.0 ± 0.1 | 2.5 ± 0.4 | 3.4 ± 0.3 | 9.7 ± 0.3 | 18.2 ± 1.2 |
| 17 | Tacrolimus | 1.2 ± 0.6 | 7.8 ± 0.4 | 5.1 ± 0.6 | ND | ND |
| 18 | Tobramycin | 1.0 ± 0.2 | 0.5 ± 0.1 | 0.6 ± 0.1 | 0.9 ± 0.3 | 25.5 ± 1.5 |
| 19 | Acetaminophen | 1.0 ± 0.1 | 0.8 ± 0.3 | 1.2 ± 0.2 | 0.5 ± 0.1 | 0.1 ± 0.0 |
| 20 | Ethylene glycol | 1.1 ± 0.3 | 0.9 ± 0.0 | 1.5 ± 0.4 | 2.0 ± 1.6 | 1.7 ± 0.4 |
| 21 | Lincomycin | 1.0 ± 0.1 | 1.2 ± 1.2 | 1.2 ± 0.3 | 2.4 ± 0.9 | 6.1 ± 0.5 |
| 22 | Lindane | 1.0 ± 0.2 | 27.4 ± 6.2 | 46.2 ± 22.4 | 85.0 ± 19.1 | 4.2 ± 1.3 |
| 23 | Lithium chloride | 1.1 ± 0.3 | 0.8 ± 0.2 | 1.2 ± 0.0 | 1.5 ± 0.1 | 27.4 ± 2.0 |
| 24 | Phenacetin | 1.1 ± 0.7 | 23.3 ± 3.1 | 11.1 ± 0.8 | 7.7 ± 4.7 | 6.4 ± 2.1 |
| 25 | Valacyclovir | 1.0 ± 0.2 | 1.5 ± 0.1 | 1.4 ± 0.1 | 1.0 ± 0.5 | 32.5 ± 4.1 |
| 26 | Vancomycin | 1.0 ± 0.2 | 0.7 ± 0.0 | 0.6 ± 0.2 | 2.9 ± 0.2 | 98.5 ± 4.5 |
| 27 | Acarbose | 1.0 ± 0.0 | 0.5 ± 0.1 | 0.6 ± 0.2 | 0.4 ± 0.1 | 1.6 ± 0.2 |
| 28 | Glycine | 1.2 ± 0.5 | 1.6 ± 0.6 | 3.1 ± 1.5 | 2.5 ± 0.6 | 4.9 ± 1.9 |
| 29 | Melatonin | 1.0 ± 0.1 | 9.8 ± 2.4 | 6.9 ± 1.0 | 1.9 ± 0.9 | ND |
| 30 | Ribavirin | 1.0 ± 0.1 | 1.1 ± 0.4 | 0.5 ± 0.1 | 0.2 ± 0.0 | 0.2 ± 0.0 |

The cells were treated on the evening of d8 with the compounds listed on the left in Tables 2 and 3. Group 1 (nephrotoxicants that are directly toxic for PTC) comprises compounds 1-18. Group 2 (compounds that are not toxic for PTC) comprises compounds 19-30. Compounds 19-26 are nephrotoxicants that do not damage PTC directly and compounds 27-30 are not nephrotoxic in humans. Each compound was applied at concentrations of 1 µg/ml, 10 µg/ml, 100 µg/ml and 1,000 µg/ml. 0 represents the vehicle control (compound concentration: 0 µg/ml). IL6 and IL8 expression levels were determined by qPCR on the morning of d9. In some cases IL6 or IL8 expression levels could not be determined (ND) due to massive cell death: The results show the mean+/−s.d. (n=3). All results were normalized to the respective vehicle controls and the means of the vehicle controls were set to 1.

Then, for each compound, log-logistic models were used to estimate its IL6 and IL8 dose response curves, and determined the responses at the highest tested doses from the estimated curves (IL6max and IL8max, FIG. 10a). Based on these features, an automated classifier called support vector machine (SVM) was used to classify the compounds into Groups 1 and 2.

Finally, a cross validation procedure was used to randomly divide all the compounds into two non-overlapping subsets, train a classifier on one of the subsets, and tested the trained classifier on the other unused subset. It was found that HPTC-like cells have a prediction accuracy that is similar to the mean value obtained with HPTC (cross-validated balanced accuracy=88% vs. 87%, Table 4). We also trained a final SVM classifier using all the compounds, and found that the classifier can perfectly separate the two groups (final accuracy=100%, FIG. 10b) in case of HPTC-like cells and two of the three batches of HPTC.

TABLE 4

Cross-validated nephrotoxicity prediction performance. $IL6_{max}$ and $IL8_{max}$

|  | Sensitivity | Specificity | Balanced Accuracy |
|---|---|---|---|
| HPTC1 | 94% | 95% | 95% |
| HPTC2 | 82% | 84% | 83% |
| HPTC3 | 85% | 84% | 84% |
| Mean | 87% | 88% | 87% |
| HPTC-like | 85% | 91% | 88% |

The performance of SVM classifiers was estimated using a standard 3-fold cross validation procedure with 10 random trials. The mean values shown are the averages of three batches of HPTC (HPTC1, HPTC2, HPTC3) originating from different donors. Mean HPTC values and values obtained with HPTC-like cells are printed in bold to facilitate comparisons.

Together, these results show that hiPSC-derived HPTC-like cells in combination with the SVM classifier could be used to predict FTC-specific nephrotoxicity of drugs.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

Fisel, P., Renner, O., Nies, A. T., Schwab, M. & Schaeffeler, E. Solute carrier transporter and drug-related nephrotoxicity: the impact of proximal tubule cell models for preclinical research. *Expert Opin Drug Metab Toxicol* 10, 395-408 (2014).

Tiong, H. Y. et al. Drug-Induced Nephrotoxicity: Clinical Impact and Preclinical in Vitro Models. *Mol Pharm* 11, 1933-1948 (2014).

Naughton, C. A. Drug-induced nephrotoxicity. *Am Fam Physician* 78, 743-750 (2008).

Redfern, W. S. Impact and frequency of different toxicities throughout the pharmaceutical life cycle. *The Toxicologist* 114, 1081 (2010).

Li, Y. et al. An in vitro method for the prediction of renal proximal tubular toxicity in humans. *Toxicol Res* 2, 352-362 (2013).

Narayanan, K. et al. Human embryonic stem cells differentiate into functional renal proximal tubular-like cells. *Kidney Int* 83, 593-603 (2013).

Li, Y. et al. Identification of nephrotoxic compounds with embryonic stein cell derived human renal proximal tubular-like cells. *Mol Pharm* 11, 1982-1990 (2014).

Kang, M. & Han, Y. M. Differentiation of human pluripotent stein cells into nephron progenitor cells in a serum and feeder free system. *PLoS One* 9, e94888 (2014).

Lam, A. Q. et al. Rapid and Efficient Differentiation of Human Pluripotent Stem Cells into Intermediate Mesoderm That Forms Tubules Expressing Kidney Proximal Tubular Markers. *J Am Soc Nephrol* 25, 1211-1225 (2014).

Mae, S. et al. Monitoring and robust induction of nephrogenic intermediate mesoderm from human pluripotent stem cells. *Nat Commun* 4, 1367 (2013).

Taguchi, A. et al. Redefining the in vivo origin of metanephric nephron progenitors enables generation of complex kidney structures from pluripotent stem cells. *Cell Stem Cell* 14, 53-67 (2014).

Takasato, M. et al. Directing human embryonic stein cell differentiation towards a renal lineage generates a self-organizing kidney. *Nat Cell Biol* 16, 118-126 (2014).

Xia, Y. et al. Directed differentiation of human pluripotent cells to ureteric bud kidney progenitor-like cells. *Nat Cell Biol* 15, 1507-1515 (2013).

Showell, C., Binder, O. & Conlon, F. L. T-box genes in early embryogenesis. *Dev Dyn* 229, 201-218 (2004).

Mugford, J. W., Sipila, P., McMahon, J. A. & McMahon, A. P. Osr1 expression demarcates a multi-potent population of intermediate mesoderm that undergoes progressive restriction to an Osr1-dependent nephron progenitor compartment within the mammalian kidney. *Dev Biol* 324, 88-98 (2008).

Kobayashi, A. et al. Six2 defines and regulates a multipotent self-renewing nephron progenitor population throughout mammalian kidney development. *Cell Stem Cell* 3, 169-181 (2008).

Kreidberg, J. A. WT1 and kidney progenitor cells. *Organogenesis* 6, 61-70 (2010).

Vainio, S. & Lin, Y. Coordinating early kidney development: lessons from gene targeting. *Nat Rev Genet* 3, 533-543 (2002).

Mugford, J. W., Sipila, P., Kobayashi, A., Behringer, R. R. & McMahon, A. P. Hoxd11 specifies a program of metanephric kidney development within the intermediate mesoderm of the mouse embryo. *Dev Biol* 319, 396-405 (2008).

Thomson, R. B. et al. Isolation and cDNA cloning of Ksp-cadherin, a novel kidney specific member of the cadherin multigene family. *J Biol Chem* 270, 17594-17601 (1995).

Maunsbach, A. B. et al. Aquaporin-1 water channel expression in human kidney. *J Am Soc Nephrol* 8, 1-14 (1997).

Hanigan, M. H. & Frierson, H. F., Jr. Immunohistochemical detection of gammaglutamyl transpeptidase in normal human tissue. *J Histochem Cytochem* 44, 1101-1108 (1996).

Elberg, G., Guruswamy, S., Logan, C. J., Chen, L. & Turman, M. A. Plasticity of epithelial cells derived from human normal and ADPKD kidneys in primary cultures. *Cell Tissue Res* 331, 495-508 (2008).

Kusaba, T., Lalli, M., Kramann, R., Kobayashi, A. & Humphreys, B. D. Differentiated kidney epithelial cells repair injured proximal tubule. *Proc Natl Acad Sci USA* 111, 1527-1532 (2014).

Fan, J. M. et al. Transforming growth factor-beta regulates tubular epithelial myofibroblast transdifferentiation in vitro. *Kidney Int* 56, 1455-1467 (1999).

Zhang, H. et al. Generation of easily accessible human kidney tubules on two dimensional surfaces in vitro. *J Cell Mol Med* 15, 1287-1298 (2011).

Palena, C. et al. The human T-box mesodermal transcription factor Brachyury is a candidate target for T-cell-mediated cancer immunotherapy. *Clin Cancer Res* 13, 2471-2478 (2007).

Biber, J., Hernando, N., Forster, I. & Murer, H. Regulation of phosphate transport in proximal tubules. *Pflugers Arch* 458, 39-52 (2009).

Burckhardt, G. Drug transport by Organic Anion Transporters (OATs). *Pharmacol Ther* 136, 106-130 (2012).

Miller, R. P., Tadagavadi, R. K., Ramesh, G. & Reeves, W. B. Mechanisms of Cisplatin nephrotoxicity. *Toxins (Basel)* 2, 2490-2518 (2010).

Davies, J. A. & Fisher, C. E. Genes and proteins in renal development. *Exp Nephrol* 10, 102-113 (2002).

Mishra, J. et al. Identification of neutrophil gelatinase-associated lipocalin as a novel early urinary biomarker for ischemic renal injury. *J Am Soc Nephrol* 14, 2534-2543 (2003).

Vanmassenhove, J., Vanholder, R., Nagler, E. & Van Biesen, W. Urinary and serum biomarkers for the diagnosis of acute kidney injury: an in-depth review of the literature. *Nephrol Dial Transplant* 28, 254-273 (2013).

Bonventre, J. V. Kidney injury molecule-1 (KIM-1): a urinary biomarker and much more. *Nephrol Dial Transplant* 24, 3265-3268 (2009).

Wallin, A., Zhang, G., Jones, T. W., Jaken, S. & Stevens, J. L. Mechanism of the nephrogenic repair response. Studies on proliferation and vimentin expression after 35S-1,2-dichlorovinyl-L-cysteine nephrotoxicity in vivo and in cultured proximal tubule epithelial cells. *Lab Invest* 66, 474-484 (1992).

Weiland, C., Ahr, H. J., Vohr, H. W. & Ellinger-Ziegelbauer, H. Characterization of primary rat proximal tubular cells by gene expression analysis. *Toxicol In Vitro* 21, 466-491 (2007).

Chabardes-Garonne, D. et al. A panoramic view of gene expression in the human kidney. *ProC Natl Acad Sci USA* 100, 13710-13715 (2003).

Simon, D. B. et al. Gitelman's variant of Bartter's syndrome, inherited hypokalaemic alkalosis, is caused by mutations in the thiazide-sensitive Na—Cl cotransporter. *Nat Genet* 12, 24-30 (1996).

Carota, I. et al. Localization and functional characterization of the human NKCC2 isoforms. *Acta Physiol (Oxf)* 199, 327-338 (2010).

Vyletal, P., Bleyer, A. J. & Kmoch, S. Uromodulin biology and pathophysiology—an update. *Kidney Blood Press Res* 33, 456-475 (2010).

Berndt, W. O. The role of transport in chemical nephrotoxicity. *Toxicol Pathol* 26, 52-57 (1998).

Muller, F. & Fromm, M. F. Transporter-mediated drug-drug interactions. *Pharmacogenomics* 12, 1017-1037 (2011).

Yang, L. et al. Aristolochic acid nephropathy: variation in presentation and prognosis. *Nephrol Dial Transplant* 27, 292-298 (2012).

Cortes, C. & Vapnik, V. Support-vector networks. *Machine Learning* 20, 273-297 (1995).

Ekins, S. Progress in computational toxicology. *J Pharmacol Toxicol Methods* 69, 115-140 (2014).

Omer, A., Singh, P., Yadav, N. K. & Singh, R. K. An overview of data mining algorithms in drug induced toxicity prediction. *Mini Rev Med Chem* 14, 345-354 (2014).

Zhang, J. H., Chung, T. D. & Oldenburg, K. R. A Simple Statistical Parameter for Use in Evaluation and Validation of High Throughput Screening Assays. *J Biomol Screen* 4, 67-73 (1999).

Ritz, C. & Streibig, R. Bioassay analysis using R. *J. Stat. Software* 12, 1-22 (2005).

Hastie, T., Tibshirani, R. & Friedman, J. (eds.) The Elements of Statistical Learning: Data Mining, Inference, and Prediction, Edn. 2nd (Springer Science+Business Media LLC, Philadelphia, Pa., USA; 2009).

What is claimed is:

1. A population of proximal tubular cell (PTC)-like cells in which 90% or greater of the cells express AQP1, the population of PTC-like cells expressing MDR1, but at a lower level than is expressed in PTCs, and expressing one or both of Oct3/4 and DNM3 TB, but at a level that is at least 50% lower than is expressed in undifferentiated induced pluripotent stem cells (iPSCs), and the population of PTC-like cells differentiated from a population of iPSCs seeded at a density of about 5 000 to about 10 000 viable cells/cm², in renal epithelial cell culture medium in the presence of one or more extracellular matrix molecule, bone morphogenic protein 2, and bone morphogenic protein 7, for a period of from about 7 to about 10 days.

2. The population of PTC-like cells of claim 1, the period is from about 8 to about 10 days.

3. The population of PTC-like cells of claim 1, wherein about 90% or greater of the cells express AQP1, PEPT1, OAT3 and GLUT1.

4. A bioengineered tissue graft comprising a matrix seeded with the population of PTC-like cells of claim 1.

5. The tissue graft of claim 4, wherein the matrix is a decellularized matrix.

6. The population of PTC-like cells of claim 1, wherein about 90% or greater of the cells in the population of PTC-like cells express AQP1, PEPT1, GLUT1, and URO10.

* * * * *